United States Patent
Derive et al.

(10) Patent No.: US 10,948,498 B2
(45) Date of Patent: Mar. 16, 2021

(54) METHODS AND KITS FOR PREDICTING THE RISK OF HAVING A CARDIOVASCULAR DISEASE OR EVENT

(71) Applicants: INOTREM, Nancy (FR); APHP (ASSISTANCE PUBLIQUE—HÔPITAUX DE PARIS), Paris (FR); INSERM (INSTITUT NATIONAL DE LA SANTÉ ET DE LA RECHERCHE MÉDICALE), Paris (FR); UNIVERSITÉ DE LORRAINE, Nancy (FR)

(72) Inventors: Marc Derive, Cahvigny (FR); Sebastien Gibot, Remereville (FR); Hafid Ait-Oufella, Charenton-le-Pont (FR); Amir Boufenzer, Nancy (FR); Tabasomme Simon, Paris (FR); Nicolas Danchin, Paris (FR)

(73) Assignees: INOTREM, Nancy (FR); APHP (Assistance Publique-Hôpitaux de Paris), Paris (FR); INSERM (Institut National de la Santé et de la Recherche Médicale), Paris (FR); Université de Lorraine, Nancy (FR)

( * ) Notice: Subject to any disclaimer, the term of this patent is extended or adjusted under 35 U.S.C. 154(b) by 331 days.

(21) Appl. No.: 14/910,715

(22) PCT Filed: Aug. 8, 2014

(86) PCT No.: PCT/EP2014/067120
§ 371 (c)(1),
(2) Date: Feb. 8, 2016

(87) PCT Pub. No.: WO2015/018936
PCT Pub. Date: Feb. 12, 2015

(65) Prior Publication Data
US 2016/0187352 A1    Jun. 30, 2016

Related U.S. Application Data

(60) Provisional application No. 61/863,987, filed on Aug. 9, 2013.

(30) Foreign Application Priority Data

Jan. 31, 2014 (EP) .................................. 14153519

(51) Int. Cl.
*G01N 31/00* (2006.01)
*G01N 33/53* (2006.01)
(Continued)

(52) U.S. Cl.
CPC ....... *G01N 33/6872* (2013.01); *G01N 33/566* (2013.01); *G01N 2333/70596* (2013.01);
(Continued)

(58) Field of Classification Search
None
See application file for complete search history.

(56) References Cited

U.S. PATENT DOCUMENTS 8,021,836 B2 *    9/2011    Kolopp-Sarda .... G01N 33/6893
435/6.15

FOREIGN PATENT DOCUMENTS

| WO | 2008/088849 A2 | 7/2008 |
| WO | 2009/013319 A1 | 1/2009 |
| WO | 2012106152 A1 | 8/2012 |

OTHER PUBLICATIONS

Dewan et al. Increased levels of soluble triggering receptor expressed on myeloid cells sTREM1 in ICU patients with cardiovascular disease and associated organ dysfunction. Crit Care. 2011; 15(Suppl 1):P280.*

(Continued)

Primary Examiner — Lisa V Cook
(74) Attorney, Agent, or Firm — W & C IP

(57) ABSTRACT

A cardiovascular event or disease is prevented or treated in a subject by measuring the expression level of soluble Triggering Receptors Expressed on Myeloid cells-1
(Continued)

(sTREM-1) level in a sample from the subject and comparing it to a reference level. Based on this comparison, subjects that are at risk of having or developing a cardiovascular event or disease are identified, and administered a suitable therapy.

9 Claims, 4 Drawing Sheets

Specification includes a Sequence Listing.

(51) Int. Cl.
 *G01N 33/68* (2006.01)
 *G01N 33/566* (2006.01)
(52) U.S. Cl.
 CPC . *G01N 2800/323* (2013.01); *G01N 2800/324* (2013.01); *G01N 2800/50* (2013.01); *G01N 2800/52* (2013.01)

(56) References Cited

OTHER PUBLICATIONS

Dewan et al. Crit Care. 2011; 15(Suppl 1):P280.*
Hanssen et al. Heart, 2012, vol. 98, pp. 699-705.*
Dewan et al. Critical Care, 2011; 15 (Suppl. 1) P280; published online Mar. 11, 2011 (Year: 2011).*
Lemarie et al. European Heart Journal, vol. 34, Issue suppl 1, Aug. 1, 2013, 3691 (Year: 2013).*
Tao et al. Mediators of Inflammation (2013) vol. 2013, Article ID 819246, 6 pages (Year: 2013).*
Hanssen et al. Heart, 2012, vol. 98, pp. 699-705 (Year: 2012).*
Conquy et al. (Shock, vol. 28., No. 4, pp. 406-410, 2007) (Year: 2007).*
Hermus et al., "Novel serum biomarkers in carotid artery stenosis: Useful to identify the vulnerable plaque?", Clinical Biochemistry, Aug. 24, 2011, pp. 1292-1298, vol. 44, No. 16, Elsevier Inc, US.
Dopheide et al., "Critical limb ischaemia is characterised by an increased production of whole blood reactive oxygen species and expression of TREM-1 on neutrophils", Atherosclerosis, Aug. 1, 2013, pp. 396-403, vol. 229, No. 2.
Ait-Oufella et al "Recent advances on the role of cytokines in atherosclerosis" Arterioscler Thromb Vasc Biol. 2011, 31(5):969-979.
Libby "Inflammation in atherosclerosis" Nature. 2002, 420(6917):868-874.
Sabatine et al. "Relationship Between Baseline White Blood Cell Count and Degree of Coronary Artery Disease and Mortality in Patients With Acute Coronary Syndromes" J. Am. Coll. Cardiol. 2002, 40:1761-1768.
Derive et al. "Triggering receptor expressed on myeloid cells-1 as a new therapeutic target during inflammatory diseases" Self Nonself. 2010, 1:225-230.
Derive et al. "Soluble Trem-like Transcript-1 Regulates Leukocyte Activation and Controls Microbial Sepsis" J Immunol. 2012, 188(11):5585-92.
Gomez-Pina et al. "Metalloproteinases Shed TREM-1 Ectodomain from Lipopolysaccharide-Stimulated Human Monocytes" J Immunol. 2007, 179(6):4065-73.
Hanssen et al. "French Registry on Acute ST-elevation and non ST-elevation Myocardial Infarction 2010. FAST-MI 2010" Heart. 2012, 98(9):699-705.
Gingras et al, "TREM-1, MDL-1, and DAP12 expression is associated with a mature stage of myeloid development" Mol Immunol. 2002, 38(11):817-24.
Gomez-Pina et al, "Role of MMPs in orchestrating inflammatory response in human monocytes via a TREM-1-PI3K-NF-kB pathway" J Leukoc Biol. 2012, 91(6):933-45.
Swirski and Nahrendorf, "Leukocyte Behavior in Atherosclerosis, Myocardial Infarction, and Heart Failure" Science. 2013, 339: 161-166.
Dewan S et al., Increased levels of soluble triggering receptor expressed on myeloid cells sTREM1 in ICU patients with cardiovascular disease and associated organ dysfunction. Crit Care. 2011; 15(Suppl 1): P280.

\* cited by examiner

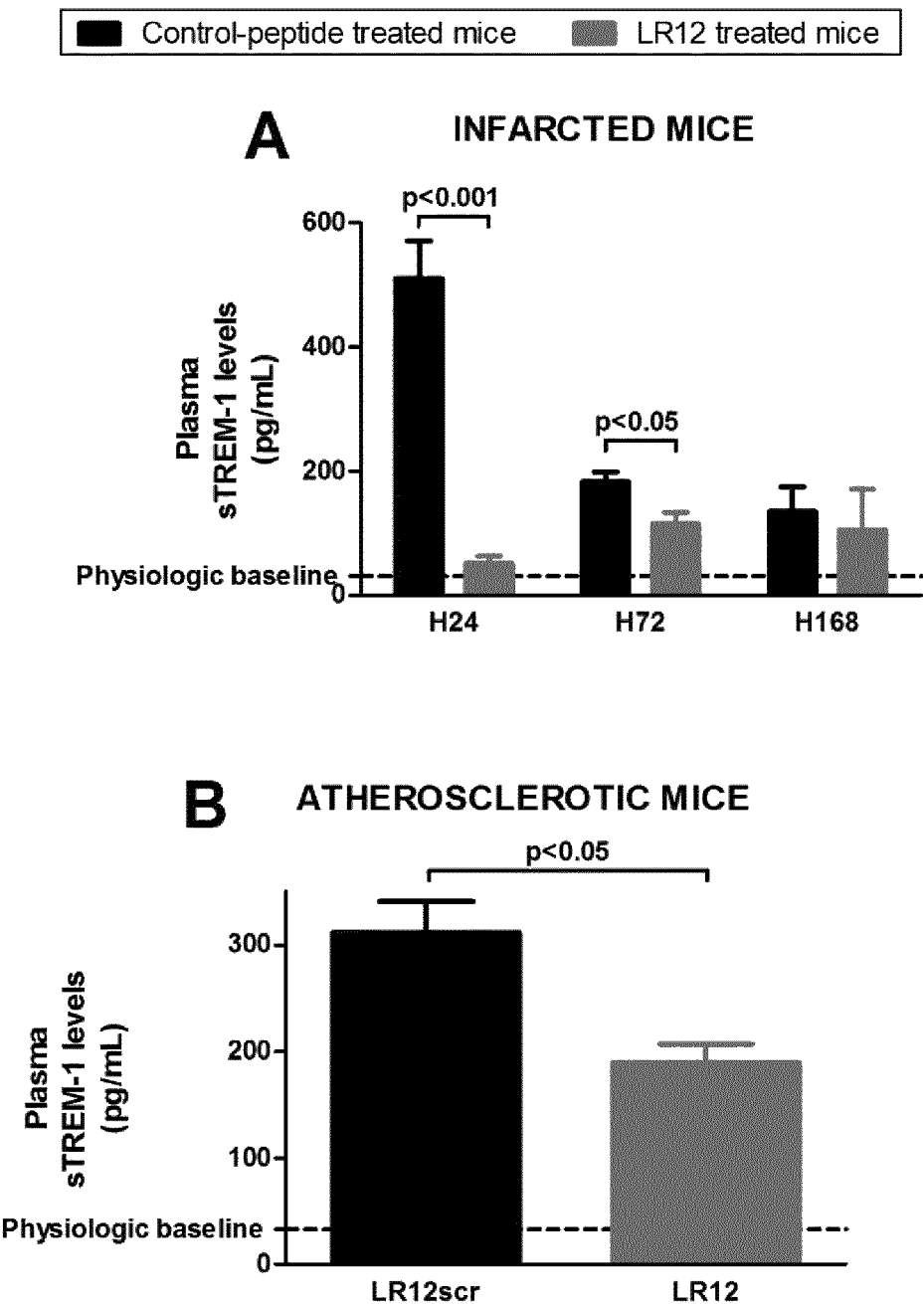
FIG. 4A-B

METHODS AND KITS FOR PREDICTING THE RISK OF HAVING A CARDIOVASCULAR DISEASE OR EVENT

CROSS-REFERENCE TO RELATED APPLICATIONS

This application is a Rule 371 national stage filing from international application PCT/EP2014/067120 filed Aug. 8, 2014, which claimed benefit of the priority date of U.S. Provisional 61/863,987 filed Aug. 9, 2013 and European Patent Application 14153519.5 filed Jan. 31, 2014.

FIELD OF INVENTION

The present invention relates to methods and kits for predicting the risk of a subject of having a cardiovascular event by measuring the level of soluble TREM-1 in a sample.

BACKGROUND OF INVENTION

Atherosclerosis gives rise to cerebrovascular disease and coronary artery disease through a slowly progressing lesion formation and luminal narrowing of arteries. Upon plaque rupture and thrombosis, these most common forms of cardiovascular disease manifest as acute coronary syndrome (ACS), myocardial infarction or stroke. Human and animal studies have established that atherosclerosis is driven by a chronic inflammatory process within the arterial wall initiated mainly in response to endogenously modified structures, particularly oxidized lipoproteins that stimulate both innate and adaptive immune responses. The innate response is instigated by the activation of both vascular cells and monocytes/macrophages, subsequently an adaptive immune response develops against an array of potential antigens presented to effector T lymphocytes by antigen-presenting cells (Ait-Oufella, H. et al. 2011. Arterioscler. Thromb. Vasc. Biol. 31: 969-979.). Genetically modified mouse models taught us that circulating monocytes were recruited into the vascular wall by chemokines and then become macrophages and lipid-loaded foam cells. Intima macrophages promote plaque development through cytokine release, inflammation amplification and plaque destabilization through protease production and apoptosis accumulation (Libby, P. et al. 2011. Nature 473: 317-325.). Monocyte/macrophage are stimulated by several mediators named PAMPs (for Pathogen Associated Molecular Patterns) that interact with PRRs (for Pathogen Recognition Receptors). Several PRRs are implicated in the physiopathology of atherosclerosis. For example, Toll-like receptors are expressed in human and animal atherosclerotic lesions.

Myocardial or cerebral infarction exemplifies a complex clinical syndrome that results from a harmful and damaging, permanent or transitional, ischemia. This is usually caused by coronary/cerebral artery occlusion, resulting in an imbalance between oxygen supply and demand. Myocardial infarction is associated with a multiphasic inflammatory response. Initial ischemia induces necrosis, formation of free radical oxygen species, complement activation, and a cytokine cascade initiated by TNF-alpha release. Reperfusion phase of the infarcted area is associated with an increased and accelerated inflammatory reaction responsible for leucocytes recruitment at the site of ischemia. Recruited leucocytes also participate to an in situ and systemic release of inflammatory mediators, leading in fine to a hyperactivated inflammatory state, responsible for pathophysiological consequences of infarction.

In summary, there is a large body of evidence showing that innate immunity, especially monocytes/macrophages and neutrophils, plays a crucial role in the pathophysiology of atherosclerosis and post-ischemic cardiac tissue remodelling. Myocardial infarction (MI) induces high levels of blood circulating monocytes during several weeks. Elevated levels of circulating monocytes provide an expanded pool of inflammatory cells available for recruitment to growing arterial lesions, potentially promoting plaque rupture. Indeed, leukocytosis after MI predicts an increased risk of re-infarction and death (Swirski F K. And Nahrendorf M. 2013. Science. 339: 161-166., Sabatine, M. S et al. 2002. J. Am. Coll. Cardiol. 40: 1761-1768). In facts, MI increases inflammation in atherosclerotic plaques at a distance, thus accelerating chronic atherosclerosis, and innate immune cells are a driving force for this phenomenon.

TREM-1 (Triggering Receptors Expressed on Myeloid cells-1) is an immunoreceptor expressed by innate immune cells (monocyte/macrophages and neutrophils). TREM-1 activation leads to cytokines and chemokines production (TNF-$\alpha$, IL-6, IL-8, MCP-1 and -3, MIP-1$\alpha$ ... ) along with rapid neutrophil degranulation and oxidative burst (Derive, M. et al. 2010. Self Nonself 1: 225-230, Derive, M. et al. 2012. J. Immunol. Baltim. Md. 1950). The TREM-1 function is to modulate/amplify rather than to activate/initiate inflammation by synergizing with PRRs (including TLRs) in order to trigger an exuberant immune response.

C-Reactive Protein (CRP) is widely used in cardiovascular event diagnostic tests. However, it is not recognized in the art as a very specific prognostic indicator.

Current diagnostic procedures have not been entirely satisfactory, for example in identifying individuals at risk for certain outcomes. Diagnostic and predictive methods and systems are needed for coronary artery disease, such as those that are non-invasive, sensitive, and reliable for the assessment and prediction of adverse cardiovascular outcomes, particularly for people at risk for CAD and its consequences.

The present invention thus aims at providing a novel method for identifying a subject at risk of having or developing a cardiovascular event or disease.

SUMMARY

One object of the invention is a method for identifying a subject at risk of having or developing a cardiovascular event or disease or at risk of all-cause death, said method comprising measuring the level of sTREM-1 in a sample from the subject.

Another object of the invention is a method for stratifying a subject at risk of having or developing a cardiovascular event or disease or at risk of all-cause death, said method comprising measuring the level of sTREM-1 in a sample from the subject.

Another object of the invention is a method for assessing the severity of a cardiovascular event or disease in a subject, said method comprising measuring the level of sTREM-1 in a sample from the subject.

In one embodiment, the sTREM-1 level is compared to a reference value.

In one embodiment; a sTREM-1 level higher than the reference value is indicative of a risk of having or developing a cardiovascular event or disease or a risk of all-cause death.

In one embodiment, the sample is a blood sample.

In one embodiment, said cardiovascular event is myocardial infarction. In another embodiment, said cardiovascular event is atherosclerosis.

Another object of the invention is a method for monitoring a cardiovascular event or disease in a subject in need thereof, said method comprising measuring the level of sTREM-1 in a sample from the subject.

Another object of the invention is a method for monitoring the effectiveness of a therapy administered to a subject suffering or having suffered of a cardiovascular event or disease, said method comprising measuring the level of sTREM-1 in a sample from the subject. In one embodiment, the level of sTREM-1 is compared to a personalized reference value of the subject. Preferably, the personalized reference value of the subject is the level of sTREM-1 measured in a sample obtained from the subject before or at the beginning of the therapy.

DEFINITIONS

In the present invention, the following terms have the following meanings:

"Cardiovascular event" is used interchangeably herein with the term "cardiac event", "acute arteriovascular event", or "arteriovascular event" and refers to sudden cardiac death, acute coronary syndromes such as, but not limited to, plaque rupture, myocardial infarction, unstable angina, as well as non-cardiac acute arteriovascular events such as blood clots of the leg, aneurysms or aneurysm progression, stroke and other arteriovascular ischemic events where arteriovascular blood flow and oxygenation is transiently or permanently interrupted.

"Cardiovascular disease" or "arteriovascular disease" as defined herein is a general term used to classify numerous conditions affecting the heart, heart valves, blood, and vasculature of the body and encompasses any disease affecting the heart or blood vessels, including, but not limited to, Metabolic Syndrome, Syndrome X, atherosclerosis, atherothrombosis, coronary artery disease, stable and unstable angina pectoris, stroke, diseases of the aorta and its branches (such as aortic stenosis, thrombosis or aortic aneurysm), peripheral artery disease, peripheral vascular disease, cerebrovascular disease, and including, without limitation, any transiently or permanently ischemic arteriovascular event. Arteriovascular disease as used herein is meant to most commonly refer to the ischemic or pro-ischemic disease, rather than generally to non-ischemic disease. As used herein, "atherosclerosis" and "atherothrombosis" refer to systemic inflammatory disease states associated with complex inflammatory responses to multifaceted vascular pathologies involving inflammatory activation of the endothelium, inflammatory leukocytes as a source of thrombogenic stimuli, smooth muscle cells as a source of procoagulants and amplifier of the inflammatory response during thrombosis, and platelets as mediators of inflammation and thrombosis. Arteries harden and narrow due to build up of a material called "plaque" on their inner walls. As the plaque develops and increases in size, the insides of the arteries get narrower ("stenosis") and less blood can flow through them. Stenosis or plaque rupture may cause partial or complete occlusion of the affected vasculature. Tissues supplied by the vasculature are thus deprived of their source of oxygenation (ischemia) and cell death (necrosis) can occur. "CAD" or "coronary artery disease" is an arteriovascular disease which occurs when the arteries that supply blood to the heart muscle (the coronary arteries) become atherosclerotic, calcified and/or narrowed. Eventually, blood flow to the heart muscle is reduced, and, because blood carries much-needed oxygen, the heart muscle is not able to receive the amount of oxygen it needs, and often undergoes necrosis. CAD encompasses disease states such as acute coronary syndromes (ACS), myocardial infarction (heart attack), angina (stable and unstable), and atherosclerosis and atherothrombosis that occurs in the blood vessels that supply the heart with oxygen-rich blood. "CVD" or "cerebrovascular disease" is an arteriovascular disease in the blood vessels that feed oxygen-rich blood to the face and brain, such as atherosclerosis and atherothrombosis. This term is often used to describe "hardening" of the carotid arteries, which supply the brain with blood. It is a common comorbid disease with CAD and/or PAD (peripheral artery disease). It is also referred to as an ischemic disease, or a disease that causes a lack of blood flow. CVD encompasses disease states such as cerebrovascular ischemia, acute cerebral infarction, stroke, ischemic stroke, hemorrhagic stroke, aneurysm, mild cognitive impairment (MCI) and transient ischemic attacks (TIA). Ischemic CVD is believed to closely relate to CAD and PAD; non-ischemic CVD may have multiple pathophysiologies. An estimated 5 million Americans are the survivors of past diagnosed acute CVD events, with an estimated 700 thousand acute CVD events occurring each year. As disclosed herein, subjects deemed to be at low risk or no risk of CVD based on clinical assessments of traditional arteriovascular disease risk factors, or without symptoms such as TIAs, MCI or severe headache, may still be at risk for an acute CVD event. "PAD" or "peripheral artery disease" encompasses disease states such as atherosclerosis and atherothrombosis that occur outside the heart and brain. It is a common comorbid disease with CAD. Subjects who are deemed to be at low risk or no risk of PAD based upon an assessment of traditional risk factors of PAD (or arteriovascular disease), or who are asymptomatic for PAD or an arteriovascular disease may nevertheless be at risk for an arteriovascular event, even in the absence of claudication. Claudication can be defined as pain or discomfort in the muscles of the legs occurring due to a decreased amount of blood flowing to a muscle from narrowing of the peripheral arteries, producing ischemia and often arterial occlusion, causing skeletal muscle and limb necrosis. The pain or discomfort often occurs when walking and dissipates under resting conditions (intermittent claudication). Pain, tightness, cramping, tiredness or weakness is often experienced as a result of claudication. PAD not only causes the hemodynamic alterations common in CAD, but also results in metabolic changes in skeletal muscle. When PAD has progressed to severe chronic and acute peripheral arterial occlusion, surgery and limb amputation often become the sole therapeutic options. PAD is widely considered to be an underdiagnosed disease, with the majority of confirmed diagnoses occurring only after symptoms are manifested, or only with other arteriovascular disease, and irreversible arteriovascular damage due to such ischemic events has already occurred.

"Measuring" or "measurement" or alternatively "detecting" or "detection" means assessing the presence, absence, quantity or amount (which can be an effective amount) of either a given substance within a clinical or subject-derived sample, including the derivation of qualitative or quantitative concentration levels of such substances, or otherwise evaluating the values or categorization of a subject's non-analyte clinical parameters.

"Risk" in the context of the present invention, relates to the probability that an event will occur over a specific time period, as in the conversion to arteriovascular events, and can mean a subject's "absolute" risk or "relative" risk. Absolute risk can be measured with reference to either actual observation post-measurement for the relevant time cohort, or with reference to index values developed from statistically valid historical cohorts that have been followed for the relevant time period. Relative risk refers to the ratio of absolute risks of a subject compared either to the absolute risks of low risk cohorts or an average population risk, which can vary by how clinical risk factors are assessed. Odds ratios, the proportion of positive events to negative events for a given test result, are also commonly used (odds are according to the formula p/(1−p) wherein p is the probability of event and (1−p) is the probability of no event).

A "sample" in the context of the present invention is a biological sample isolated from a subject and can include, by way of example and not limitation, bodily fluids and/or tissue extracts such as homogenates or solubilized tissue obtained from a subject. Tissue extracts are obtained routinely from tissue biopsy and autopsy material. Bodily fluids useful in the present invention include blood, urine, saliva or any other bodily secretion or derivative thereof. As used herein "blood" includes whole blood, plasma, serum, circulating epithelial cells, constituents, or any derivative of blood.

"Clinical parameters or indicia" encompasses all non-sample or non-analyte biomarkers of subject health status or other characteristics, such as, without limitation, age (Age), ethnicity (Race), gender (Sex), diastolic blood pressure (DBP) and systolic blood pressure (SBP), family history (FamHX), height (HT), weight (WT), waist (Waist) and hip (Hip) circumference, body-mass index (BMI), as well as others such as Type I or Type II Diabetes Mellitus or Gestational Diabetes Mellitus (DM or GDM, collectively referred to here as Diabetes), and resting heart rate.

A "subject" in the context of the present invention is preferably a mammal. The mammal can be a human, non-human primate, mouse, rat, dog, cat, horse, or cow, but are not limited to these examples. Mammals other than humans can be advantageously used as subjects that represent animal models of arteriovascular disease or arteriovascular events. A subject can be male or female. A subject can be one who has been previously diagnosed or identified as having arteriovascular disease or an arteriovascular event, and optionally has already undergone, or is undergoing, a therapeutic intervention for the arteriovascular disease or arteriovascular event. Alternatively, a subject can also be one who has not been previously diagnosed as having arteriovascular disease. For example, a subject can be one who exhibits one or more risk factors for arteriovascular disease, or a subject who does not exhibit arteriovascular risk factors, or a subject who is asymptomatic for arteriovascular disease or arteriovascular events. A subject can also be one who is suffering from or at risk of developing arteriovascular disease or an arteriovascular event.

"Soluble TREM-1" (sTREM-1) as used herein relates to a soluble form of the extracellular domain of TREM-1 (accession number Q9NP99, SEQ ID NO: 1). sTREM-1 is liberated by cleavage of the extracellular domain of TREM-1. sTREM-1 may be a soluble form of TREM-1 generated by proteolytic cleavage of the membrane-bound form of TREM-1. A study by Gingras (Gingras et al, Mol Immunol 2002, March; 38(11):817-24) tried to identify the expression of an alternative mRNA TREM-1 splice variant (TREM-1sv) that might translate into a soluble receptor. But this soluble form of TREM-1 (which is a predicted protein sequence from a hypothetical nucleotide sequence) was never demonstrated to be found in humans. Later, in 2007 and 2012, Gomez-Pina (Gomez-Pina et al, J Immunol. 2007 Sep. 15; 179(6):4065-73 and Gomez-Pina et al, J Leukoc Biol. 2012 June; 91(6):933-45) demonstrated that the soluble-TREM-1 is generated by proteolytic cleavage of the membrane-anchored form of TREM-1 by metalloproteinases. Indeed, TREM-1 is a transmembrane glycoprotein that possesses an Ig-like ectodomain readily shed by MMPs to generate sTREM-1. No alternative splicing forms of TREM-1 were detected in human leucocytes.

"About" preceding a figure means plus or less 10% of the value of said figure.

DETAILED DESCRIPTION

TREM-1 (triggering Receptor Expressed on Myeloid Cells-1) is an immunoreceptor expressed by innate immune cells. Without willing to be bound to a theory, the inventors state that Nod-Like Receptors (NLRs) engagement (including Toll-Like Receptors TLRs) induce the upregulation of TREM-1 expression and its membrane exposition. Said NLRs and TLRs activation can occur either under sterile inflammatory conditions by linking Danger Associated Molecular Patterns (DAMPs) or under infectious conditions by linking Pathogen Associated Molecular Pattern (PAMPs). This activation of NLRs and TLRs induce the upregulation of metalloproteinases which in turn among a number of targets will induce the liberation of a soluble form of TREM-1 by cleavage of its extracellular domain [Gomez-Pina et al. J Immunol. 2007, 179(6):4065-73].

In one embodiment, sTREM1 has the amino acid sequence SEQ ID NO: 2, corresponding to amino acids 21 to 205 of SEQ ID NO: 1.

In another embodiment, sTREM1 has the amino acid sequence SEQ ID NO: 3, corresponding to amino acids 31 to 205 of SEQ ID NO: 1.

In one embodiment, sTREM1 is a variant of SEQ ID NO: 2 or a variant of SEQ ID NO: 3.

In one embodiment, a variant of an amino acid sequence SEQ ID NO: 2 or SEQ ID NO: 3 is an amino acid sequence comprising at least 25 contiguous amino acids, preferably at least 50, 60, 70, 80, 90, 100, 110, 120, 130, 140, 150, 160, 165, 170, 175, 180 or 185 contiguous amino acids of the amino acid sequence SEQ ID NO: 2 or SEQ ID NO: 3 respectively.

In another embodiment, a variant of an amino acid sequence SEQ ID NO: 2 or SEQ ID NO: 3 is an amino acid sequence comprising the amino acid sequence SEQ ID NO: 2 or SEQ ID NO: 3 respectively and additional amino acids in C-term or in N-term of SEQ ID NO: 2 or 3, wherein the number of additional amino acids ranges from 1 to 50, preferably from 1 to 20, more preferably from 1 to 10 amino acids, such as, for example, 1, 2, 3, 4, 5, 6, 7, 8, 9 or 10 amino acids in C-term and/or 1, 2, 3, 4, 5, 6, 7, 8, 9 or 10 amino acids in N-term.

In another embodiment, a variant of amino acid sequence SEQ ID NO: 2 or SEQ ID NO: 3 is an amino acid sequence that typically differs from SEQ ID NO: 2 or 3 in one or more substitutions, deletions, additions and/or insertions. In one embodiment, said substitutions, deletions, additions and/or insertions may affect 1, 2, 3, 4, 5, 6, 7, 8, 9, or 10 amino acids.

In another embodiment, a variant of an amino acid sequence SEQ ID NO: 2 or SEQ ID NO: 3 is an amino acid sequence of at least 25 amino acids, preferably of at least 50, 60, 70, 80, 90, 100, 110, 120, 130, 140, 150, 160, 165, 170, 175, 180 or 185 amino acids having at least 75%, 80%, 90%, 95%, or at least 96%, 97%, 98%, 99% or more identity with the amino acid sequence SEQ ID NO: 2 or SEQ ID NO: 3 respectively.

The term "identity" or "identical", when used in a relationship between the sequences of two or more polypeptides, refers to the degree of sequence relatedness between polypeptides, as determined by the number of matches between strings of two or more amino acid residues. "Identity" measures the percent of identical matches between the smaller of two or more sequences with gap alignments (if any) addressed by a particular mathematical model or computer program (i.e., "algorithms"). Identity of related polypeptides can be readily calculated by known methods. Such methods include, but are not limited to, those described in Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987; Sequence Analysis Primer, Gribskov, M. and Devereux, J., eds., M. Stockton Press, New York, 1991; and Carillo et al., SIAM J. Applied Math. 48, 1073 (1988). Preferred methods for determining identity are designed to give the largest match between the sequences tested. Methods of determining identity are described in publicly available computer programs. Preferred computer program methods for determining identity between two sequences include the GCG program package, including GAP (Devereux et al., Nucl. Acid. Res. \2, 387 (1984); Genetics Computer Group, University of Wisconsin, Madison, Wis.), BLASTP, BLASTN, and FASTA (Altschul et al., J. MoI. Biol. 215, 403-410 (1990)). The BLASTX program is publicly available from the National Center for Biotechnology Information (NCBI) and other sources (BLAST Manual, Altschul et al. NCB/NLM/NIH Bethesda, Md. 20894; Altschul et al., supra). The well-known Smith Waterman algorithm may also be used to determine identity.

In one embodiment, the variant of SEQ ID NO: 2 or SEQ ID NO: 3 is not SEQ ID NO: 1.

In one embodiment, sTREM1 is a fragment of SEQ ID NO: 2 or a fragment of SEQ ID NO: 3.

In one embodiment, a fragment of an amino acid sequence SEQ ID NO: 2 or SEQ ID NO: 3 is an amino acid sequence comprising at least 25 contiguous amino acids, preferably of at least 50, 60, 70, 80, 90, 100, 110, 120, 130, 140, 150, 160, 165, 170, 175, 180 or 185 contiguous amino acids of the amino acid sequence SEQ ID NO: 2 or SEQ ID NO: 3 respectively.

In one embodiment, sTREM1 corresponds to the extracellular fragment generated by clivage of the TREM1 sequence SEQ ID NO: 1 by a matrix metallopeptidase, preferably by the matrix metallopeptidase 9 (MMP9).

One object of the invention relates to a method for identifying a subject at risk of having or developing a cardiovascular event or a cardiovascular disease or at risk of all-cause death, said method comprising measuring the level of sTREM-1 in a sample from the subject, thereby determining whether the subject is at risk of having or developing a cardiovascular event or disease.

Another object of the invention is a method for assessing whether a subject is at risk of having or developing a cardiovascular event or a cardiovascular disease or at risk of all-cause death, said method comprising measuring the level of sTREM-1 in a sample from the subject, thereby determining whether the subject is at risk of having or developing a cardiovascular event or disease.

Another object of the invention is a method for predicting whether a subject is at risk of having or developing a cardiovascular event or a cardiovascular disease or at risk of all-cause death, said method comprising measuring the level of sTREM-1 in a sample from the subject, thereby determining whether the subject is at risk of having or developing a cardiovascular event or disease.

Another object of the invention is a method for stratifying a subject at risk of having or developing a cardiovascular event or a cardiovascular disease or at risk of all-cause death, said method comprising measuring the level of sTREM-1 in a sample from the subject, thereby determining whether the subject is at risk of having or developing a cardiovascular event or disease.

Another object of the invention is a method for assessing the severity of a cardiovascular event or a cardiovascular disease in a subject, said method comprising measuring the level of sTREM-1 in a sample from the subject, thereby determining whether the subject is at risk of having or developing a cardiovascular event or disease.

According to the invention, all-cause death refers to death occurring after a cardiovascular event or disease, such as, for example, after a first cardiovascular event or disease.

In one embodiment, the method of the invention is for identifying a subject at risk of death related to or caused by a cardiovascular event or a cardiovascular disease.

In one embodiment, the method of the invention is for assessing whether a subject is at risk of death related to or caused by a cardiovascular event or a cardiovascular disease.

In one embodiment, the method of the invention is for predicting whether a subject is at risk of death related to or caused by a cardiovascular event or a cardiovascular disease.

In one embodiment, the method of the invention is for stratifying a subject at risk of death related to or caused by a cardiovascular event or a cardiovascular disease.

In one embodiment of the invention, the subject may be a substantially healthy subject, which means that the subject has not been previously diagnosed or identified as having or suffering from a cardiovascular disease, or that has not developed a cardiovascular event.

In another embodiment, the subject may also be one that is asymptomatic for the cardiovascular disease. As used herein, an "asymptomatic" subject refers to a subject that does not exhibit the traditional symptoms of a cardiovascular disease or event, including, but not limited to, chest pain and shortness of breath for CAD, claudication for PAD, and TIAS, MCI and severe headache for CVD.

In another embodiment of the invention, the subject may be one that is at risk of having or developing a cardiovascular disease or cardiovascular event, as defined by clinical indicia such as for example: age, gender, LDL concentration, HDL concentration, triglyceride concentration, blood pressure, body mass index, CRP concentration, coronary calcium score, waist circumference, tobacco smoking status, previous history of cardiovascular disease, family history of cardiovascular disease, heart rate, fasting insulin concentration, fasting glucose concentration, diabetes status, and use of high blood pressure medication.

In another embodiment of the invention, the subject may be one that has been previously diagnosed or identified for a cardiovascular disease or cardiovascular event, such as for example chronic ischemic disorders without myocardial necrosis (for example stable or effort angina pectoris), acute ischemic disorders without myocardial necrosis (for example unstable angina pectoris), ischemic disorders with myocardial necrosis (for example ST segment evaluation myocardial infarction or non-ST segment elevation myocardial infarction).

Tissue ischemia is often defined in relative terms and occurs when the needs in oxygen exceeds the delivery of oxygen to tissues. There is an imbalance between tissue (myocardial for example) oxygen demands and supply. This condition of oxygen deprivation may be accompanied by inadequate removal of metabolites consequent to reduced perfusion. Myocardial ischemia can be diagnosed clinically (chest pain for example), biologically (increase in myeloperoxidase activity for example), metabolically, using scintigraphy, by analyzing regional wall motion disorders or by use of an electrocardiogram (typical modifications of the ST segment, upper or lower ST segment deviation, typical changes in T wave such as T wave inversion or steep symmetric or high amplitude positive T waves). Silent ischemia is typically diagnosed using scintigraphy or a 24 h electrocardiogram recording.

Stable and effort angina is typically manifested by a chest pain during exercise and slowly recovers at rest. It usually reflects tissue ischemia during exercise.

Unstable angina is a recent increase in the frequency and/or severity of stable angina, a first episode of angina, or an angina at rest.

Myocardial necrosis is typically diagnosed by an increase in myocardial enzymes (for example troponin I, troponin T, CPK) in the circulating blood.

In another embodiment of the invention, the subject may be one that shows an improvement in cardiovascular risk factors as a result of treatments and/or therapies for cardiovascular diseases. Such improvements include a reduction in body mass index, a reduction in total cholesterol, a reduction in LDL levels, an increase in HDLC levels, a reduction in systolic and/or diastolic blood pressure, or other aforementioned risk factor or combinations thereof.

In one embodiment of the invention, no onset of ischemic symptom has been diagnosed in the subject. Myocardial ischemia can be diagnosed clinically (chest pain for example), biologically (increase in myeloperoxidase activity for example), metabolically using scintigraphy, by analysing regional wall motion disorders or by use of an electrocardiogram (typical modifications of the ST segment, upper or lower ST segment deviation, typical changes in T wave such as T wave insertion or steep symmetric or high amplitude positive T waves).

In another embodiment, an onset of ischemic symptoms has been diagnosed in the subject.

In one embodiment of the invention, the sample used to measure sTREM-1 level is a blood sample, a whole blood sample, a plasma sample, a serum sample or a urine sample.

As used herein, the term "level" refers to the expression level of sTREM-1. It can refer alternatively to the transcription level of sTREM-1 or to the translation of sTREM-1. The expression level may be detected intracellularly or extracellularly. Methods for measuring the level of sTREM-1 are well-known from the skilled artisan and include, but are not limited to, RT-PCR, RT-qPCR, Northern Blot, hybridization techniques such as, for example, use of microarrays, and combination thereof including but not limited to, hybridization of amplicons obtained by RT-PCR, sequencing such as, for example, next-generation DNA sequencing (NGS) or RNA-seq (also known as "Whole Transcriptome Shotgun Sequencing") and the like, immunohistochemistry, Multiplex methods (Luminex), western blot, enzyme-linked immunosorbent assay (ELISA), sandwich ELISA, fluorescent-linked immunosorbent assay (FLISA), enzyme immunoassay (EIA), radioimmunoassay (RIA), flow cytometry (FACS) and the like.

In one embodiment of the invention, the sTREM-1 level is compared to a reference value.

In one embodiment, the reference value may be an index value or may be derived from one or more risk prediction algorithms or computed indices for the cardiovascular disease and/or cardiovascular event. A reference value can be relative to a number or value derived from population studies, including without limitation, such subjects having similar body mass index, total cholesterol levels, LDL/HDL levels, systolic or diastolic blood pressure, subjects of the same or similar age range, subjects in the same or similar ethnic group, subjects having family histories of atherosclerosis, atherothrombosis, or CAD, PAD, or CVD, or relative to the starting sample of a subject undergoing treatment for an arteriovascular disease, such as atherosclerosis, atherothrombosis, CAD, PAD, or CVD.

Such reference values can be derived from statistical analyses and/or risk prediction data of populations obtained from mathematical algorithms and computed indices of arteriovascular disease, such as but not limited to, algorithms reported in the Framingham Study, NCEP/ATP III, among others. Cardiovascular Risk Factor reference value can also be constructed and used using algorithms and other methods of statistical and structural classification.

In one embodiment, the reference value is a personalized reference, i.e. the reference value was determined using a sample obtained from the subject.

In one embodiment of the present invention, the reference value is derived from the sTREM-1 in a control sample derived from one or more subjects who are substantially healthy as defined here above. Such subjects who are substantially healthy lack traditional risk factors for a cardiovascular disease: for example, those subjects have a serum cholesterol level less than 200 mg/dl, systolic blood pressure less than or equal to 120 mm Hg, diastolic blood pressure less than or equal to 80 mm Hg, non-current smoker, no history of diagnosed diabetes, no previously diagnosed acute coronary syndrome or hypertension, among other aforementioned other risk factors, or can be verified by another invasive or non-invasive diagnostic test of cardiovascular disease known in the art, such as but not limited to, electrocardiogram (ECG), carotid B-mode ultrasound (for intima-medial thickness measurement), electron beam computed tomography (EBCT), coronary calcium scoring, multi-slice high resolution computed tomography, nuclear magnetic resonance, stress exercise testing, angiography, intra-vascular ultrasound (IVUS), other contrast and/or radioisotopic imaging techniques, or other provocative testing techniques.

In another embodiment, such subjects are monitored and/or periodically retested for a diagnostically relevant period of time ("longitudinal studies") following such test to verify continued absence from cardiovascular disease or acute cardiovascular events (disease or event free survival). Such period of time may be one year, two years, two to five years, five years, five to ten years, ten years, or ten or more years from the initial testing date for determination of the reference value. Furthermore, retrospective measurement of sTREM-1 level in properly banked historical subject samples may be used in establishing these reference values, thus shortening the study time required, presuming the subjects have been appropriately followed during the intervening period through the intended horizon of the product claim.

In another embodiment, a reference value can also be derived from the sTREM-1 level in a sample derived from one or more subject who has been previously diagnosed or identified for a cardiovascular disease or cardiovascular event by one of the above invasive or non-invasive techniques, or are at high risk for developing an cardiovascular event, or who are at high risk for developing an atherosclerotic or atherothrombotic plaque rupture, or who have suffered from an cardiovascular event or plaque rupture.

In another embodiment of the invention, a reference value can also be derived from the sTREM-1 level in a sample derived from one or more subject who shows an improvement in cardiovascular risk factors as a result of treatments and/or therapies for cardiovascular diseases. Such improvements include a reduction in body mass index, a reduction in total cholesterol, a reduction in LDL levels, an increase in HDLC levels, a reduction in systolic and/or diastolic blood pressure, or other aforementioned risk factor or combinations thereof.

In another embodiment of the invention, a reference value can also be derived from the sTREM-1 level in a sample derived from one or more subject who shows no improvement in cardiovascular risk factors as a result of treatments and/or therapies for cardiovascular diseases. Such improvements include a reduction in body mass index, a reduction in total cholesterol, a reduction in LDL levels, an increase in HDLC levels, a reduction in systolic and/or diastolic blood pressure, or other aforementioned risk factor or combinations thereof.

In one embodiment of the invention, the reference value is an index value or a baseline value. An index value or baseline value is derived from one or more subjects who do not have a cardiovascular disease, such as atherosclerosis, atherothrombosis, CAD, PAD, or CVD, or subjects who are asymptomatic for a cardiovascular disease. A baseline value can also be derived from a subject who has shown an improvement in cardiovascular risk factors (as a result of cardiovascular treatments or therapies). Such improvements include, without limitation, a reduction in body mass index, a reduction in total cholesterol, a reduction in LDL levels, an increase in HDLC levels, a reduction in systolic and/or diastolic blood pressure, or combinations thereof.

In one embodiment of the invention, said cardiovascular event or disease is Metabolic Syndrome, Syndrome X, atherosclerosis, atherothrombosis, coronary artery disease, stable and unstable angina pectoris, stroke, diseases of the aorta and its branches (such as aortic thrombosis or aortic aneurysm), peripheral artery disease, peripheral vascular disease, cerebrovascular disease, and any transiently or permanently ischemic cardiovascular event.

In one embodiment of the invention, said cardiovascular event or disease is myocardial infarction.

In another embodiment of the invention, said cardiovascular event or disease is atherosclerosis.

In one embodiment, when the level of sTREM-1 measured in a blood sample is equal or more than 265 pg/ml, 270, 275, 280, 285, 290, 295, 300, 305, 310, 315, 320, 325, 330, 335, 340, 345, 350, 360, 370, 380, 390, or 400 pg/ml, then the subject is identified as being at risk of death related to or caused by a cardiovascular event or a cardiovascular disease.

In one embodiment, subjects identified as having, or being at increased risk of developing a cardiovascular disease or cardiovascular event are chosen to receive a therapeutic regimen to slow the progression of a cardiovascular disease, or decrease or prevent the risk of developing a cardiovascular disease or a cardiovascular event.

According to the invention, the method as described here above is for monitoring a cardiovascular disease or event in a subject in need thereof.

In one embodiment of the invention, the method as described here above is for assessing the progression of a cardiovascular disease in a subject in need thereof.

In another embodiment of the invention, the method as described here above is for monitoring the effectiveness of a treatment for a cardiovascular disease. The efficacy of the treatment will be reflected by changes in the sTREM-1 level. If a treatment has a desired effect, the sTREM-1 level will be lower compared to the one obtained before the treatment. On the other hand, if a treatment has not the desired effect, the sTREM-1 level will remain high. In one embodiment, sTREM-1 level obtained before or at the beginning of the treatment is the reference value.

Therefore, the practitioner will be able to adapt the treatment (doses, regimen) to obtain a decrease of sTREM-1 level to its basal level or to the level obtained from healthy subjects.

Examples of treatments for a cardiovascular disease include, but are not limited to aspirin, clopidogrel, prasugrel, glycoprotein IIb/IIIa inhibitors, low molecular weight heparin, unfractionated heparin, fondaparinux, bivalirudin, statin, beta-blocking agents, ACE-I or ARB and the like.

In one embodiment, the treatment for a cardiovascular disease is based on the modulation of TREM-1 function, activity or expression. Examples of modulators of TREM-1 function, activity or expression include, but are not limited to, antibodies directed to TREM-1 and/or sTREM-1 or TREM-1 and/or sTREM-1 ligand, small molecules inhibiting the function, activity or expression of TREM-1, peptides inhibiting the function, activity or expression of TREM-1, siRNAs directed to TREM-1, shRNAs directed to TREM-1, antisense oligonucleotide directed to TREM-1, ribozymes directed to TREM-1 or aptamers of TREM-1.

In one embodiment, the treatment for a cardiovascular disease is a treatment with a peptide targeting sTREM-1 ligand, such as, for example, LR12 (SEQ ID NO: 4).

In another embodiment of the invention, the method as described here above is for selecting a treatment regimen for a subject diagnosed with or at risk for a cardiovascular disease or event.

Accordingly, the sTREM-1 level is measured in a sample obtained before the therapy (said level constituting the reference value) and in at least one another sample obtained during the therapy. A decrease in the sTREM-1 level is then indicative of a positive effect of the therapy on the subject. Inversely, a similar level or an increased level of sTREM-1 is indicative of the non-effectiveness of the therapy. In one embodiment of the invention, a sample is obtained from the patient before the therapy and every month during therapy, during at least 1, 2, 3, 4, 5, 6, 7, 8, 9, 10, 11, 12 months or more or during at least 1 year, 2 years, 3 years or more.

In another embodiment, the sTREM-1 level can be measured in a sample obtained at the beginning of therapy (said level constituting the reference value) and in at least one another sample obtained during the therapy. In one embodiment of the invention, a sample is obtained from the patient at the beginning of the therapy and every month during therapy, during at least 1, 2, 3, 4, 5, 6, 7, 8, 9, 10, 11, 12 months or more or during at least 1 year, 2 years, 3 years or more. In one embodiment, the beginning of the therapy corresponds to the day of the first administration of the treatment.

Another object of the invention is a kit for identifying whether a subject has or is at risk of having or developing a cardiovascular disease and/or a cardiovascular event, comprising means for measuring sTREM-1 level.

In one embodiment, said means for measuring sTREM-1 level is an antibody such as a polyclonal or monoclonal antibody.

Examples of antibodies allowing the detection of sTREM-1 include, but are not limited to, the polyclonal antibody raised against Met1-Arg200 amino acids of human TREM-1, Ref AF1278 from R&D Systems; and the monoclonal antibody raised against Ala21-Asn205 of human TREM-1, Ref MAB1278 from R&D Systems. Other non-limitative examples of antibodies allowing the detection of sTREM-1 include sTREM-1 and/or TREM-1 antibodies described in the following patents or patent applications: US2013/150559, US 2013/211050, US 2013/309239, WO2013/120553 and U.S. Pat. No. 8,106,165.

In one embodiment, said means for measuring sTREM-1 level is an Enzyme-Linked Immunosorbent Assay (ELISA).

Examples of ELISA assay include, but is not limited to, the TREM-1 Quantikine ELISA kit from R&D Systems; the Human TREM-1 DuoSet, Ref DY1278B and DY1278BE from R&DSystems, the sTREM-1 ELISA, Ref sTREM-1 ELISA from iQProducts.

Accordingly, the present invention relates to an in vitro method for identifying a subject at risk of having or developing a cardiovascular event or disease or at risk of all-cause death, or for assessing whether a subject is at risk of having or developing a cardiovascular event or disease or at risk of all-cause death, said method comprising the step of:
  i) measuring the level of sTREM-1 in a sample obtained from said subject,
  ii) comparing the level measured at step i) with a reference value wherein a difference is indicative of a risk of having or developing a cardiovascular event or disease or of all-cause death.

Accordingly, the present invention relates to an in vitro method for predicting the risk of a cardiovascular event or disease in a subject, said method comprising the step of:
  i) measuring the level of sTREM-1 in a sample obtained from said subject,
  ii) comparing the level measured at step i) with a reference value wherein a difference is indicative of a risk of having or developing a cardiovascular event or disease.

Accordingly, the present invention relates to an in vitro method for stratifying a subject at risk of having or developing a cardiovascular event or disease or at risk of all-cause death, or for assessing the severity of a cardiovascular event or cardiovascular disease in a subject said method comprising the step of:
  i) measuring the level of sTREM-1 in a sample obtained from said subject,
  ii) comparing the level measured at step i) with a reference value wherein a difference is indicative of a risk, preferably of a severe risk, of having or developing a cardiovascular event or disease.

In one embodiment of the invention, a higher level of sTREM-1 in the test sample when compared with the reference value is indicative of a risk of having or developing a cardiovascular event or disease. In one embodiment, a level of sTREM-1 in the test sample superior or equal to 10%, 20%, 30%, 40%, 50%, 60%, 70%, 80%, 90%, 100% or more compared to the reference value is indicative of a risk of having or developing a cardiovascular event or disease.

In one embodiment of the invention, a higher level of sTREM-1 in the test sample when compared with the reference value is indicative of a severe risk of having or developing a cardiovascular event or disease. In one embodiment, a level of sTREM-1 in the test sample superior or equal to about 10%, 20%, 30%, 40%, 50%, 60%, 70%, 80%, 90%, 100% or more compared to the reference value is indicative of a severe risk of having or developing a cardiovascular event or disease.

Accordingly, the present invention relates to an in vitro method for monitoring the effectiveness of a treatment for a cardiovascular disease in a subject, said method comprising the step of:
  i) measuring the level of sTREM-1 in a sample obtained from said subject,
  ii) comparing the level measured at step i) with a reference value wherein a difference is indicative of a desired effect of the treatment.

In one embodiment, the monitoring method of the invention comprises:
  i) measuring the level of sTREM-1 in a sample obtained from said subject before therapy,
  ii) measuring the level of sTREM-1 in a sample obtained from said subject during therapy, preferably very month during therapy, during at least 1, 2, 3, 4, 5, 6, 7, 8, 9, 10, 11, 12 months or more or during at least 1 year, 2 years, 3 years or more,
  iii) comparing the level measured at step ii) with the sTREM-1 level measured at step i) wherein a decrease in the sTREM-1 level is indicative of a positive effect of the therapy on the subject.

In another embodiment, the monitoring method of the invention comprises:
  i) measuring the level of sTREM-1 in a sample obtained from said subject at the beginning of therapy, preferably on the day of the first administration of the treatment,
  ii) measuring the level of sTREM-1 in a sample obtained from said subject during therapy, preferably very month during therapy, during at least 1, 2, 3, 4, 5, 6, 7, 8, 9, 10, 11, 12 months or more or during at least 1 year, 2 years, 3 years or more,
  iii) comparing the level measured at step ii) with the sTREM-1 level measured at step i) wherein a decrease in the sTREM-1 level is indicative of a positive effect of the therapy on the subject.

In one embodiment, a level of sTREM-1 in the test sample inferior or equal to about 10%, 20%, 30%, 40%, 50%, 60%, 70%, 80%, 90%, 100% or more compared to the sTREM-1 level measured before or at the beginning of the therapy is indicative of a positive effect of the therapy on the subject.

In one embodiment, the reference value is of about or at least 80 pg/mL, 100 pg/mL, or about or at least about 150, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 520, 540, 560, 580, 600, 620, 640, 660, 680, 700 pg/mL or more.

In one embodiment, the sTREM-1 levels measured in the reference population used for obtaining the reference value are classified in percentiles, wherein the sTREM-1 level values obtained by all subjects of the reference population are ranged according to their numerical value in ascending order. In one embodiment of the invention, the percentiles are percentiles of subjects, i.e. each percentile comprises the same number of subjects. Therefore, the first percentile corresponds to subjects with the lowest sTREM-1 levels, while the last percentile corresponds to subjects with the highest sTREM-1 levels.

In one embodiment, the reference value corresponds to the highest sTREM-1 level of the first percentile of the reference population.

In another embodiment, the reference value corresponds to the highest sTREM-1 level of the second, third . . . or penultimate percentile of the reference population.

In one embodiment, when three percentiles are drawn, each percentile is named a tertile. According to this embodiment, the reference value corresponds to the highest sTREM-1 level of the first or of the second tertile.

In another embodiment, when four percentiles are drawn, each percentile is named a quartile. According to this embodiment, the reference value corresponds to the highest sTREM-1 level of the first, second or third quartile.

According to the invention, the level of sTREM-1 may be measured by any known method in the art.

Typically, the methods may comprise contacting the sample with a binding partner capable of selectively interacting with sTREM-1 in the sample. In some aspects, the binding partners are antibodies, such as, for example, monoclonal antibodies or aptamers.

The aforementioned assays generally involve the binding of the partner (ie. antibody or aptamer) to a solid support. Solid supports which can be used in the practice of the invention include, but are not limited to, substrates such as nitrocellulose (e.g., in membrane or microtiter well form); polyvinylchloride (e.g., sheets or microtiter wells); polystyrene latex (e.g., beads or microtiter plates); polyvinylidine fluoride; diazotized paper; nylon membranes; activated beads, magnetically responsive beads, and the like. The level of sTREM-1 may be measured by using standard immunodiagnostic techniques, including immunoassays such as competition, direct reaction, or sandwich type assays. Such assays include, but are not limited to, agglutination tests; enzyme-labelled and mediated immunoassays, such as ELISAs; biotin/avidin type assays; radioimmunoassays; Immunoelectrophoresis; immunoprecipitation.

An exemplary biochemical test for identifying specific proteins employs a standardized test format, such as ELISA test, although the information provided herein may apply to the development of other biochemical or diagnostic tests and is not limited to the development of an ELISA test (see, e.g., Molecular Immunology: A Textbook, edited by Atassi et al. Marcel Dekker Inc., New York and Basel 1984, for a description of ELISA tests). It is understood that commercial assay enzyme-linked immunosorbant assay (ELISA) kits for various plasma constituents are available. Therefore ELISA method can be used, wherein the wells of a microtiter plate are coated with a set of antibodies which recognize sTREM-1. A sample containing or suspected of containing sTREM-1 is then added to the coated wells. After a period of incubation sufficient to allow the formation of antibody-antigen complexes, the plate(s) can be washed to remove unbound moieties and a detectably labelled secondary binding molecule added. The secondary binding molecule is allowed to react with any captured sample marker protein, the plate washed and the presence of the secondary binding molecule detected using methods well known in the art.

Measuring the level of sTREM-1 (with or without immunoassay-based methods) may also include separation of the compounds: centrifugation based on the compound's molecular weight; electrophoresis based on mass and charge; HPLC based on hydrophobicity; size exclusion chromatography based on size; and solid-phase affinity based on the compound's affinity for the particular solid-phase that is used. Once separated, said compounds may be identified based on the known "separation profile" e.g., retention time, for that compound and measured using standard techniques.

Alternatively, the separated compounds may be detected and measured by, for example, a mass spectrometer.

Typically, levels of sTREM-1 in a sample may be measured by an immunometric assay on the basis of a double-antibody "sandwich" technique, with a monoclonal antibody specific for sTREM-1.

Another object of the invention is the use of sTREM-1 as a biomarker for diagnosing a cardiovascular event or disease.

Another object of the invention is the use of sTREM-1 as a biomarker for monitoring a cardiovascular disease.

BRIEF DESCRIPTION OF THE DRAWINGS

FIG. 4 is a combination of histograms representing plasma sTREM-1 levels after a cardiac ischemic event and in atherosclerotic mice.

Figure 1:
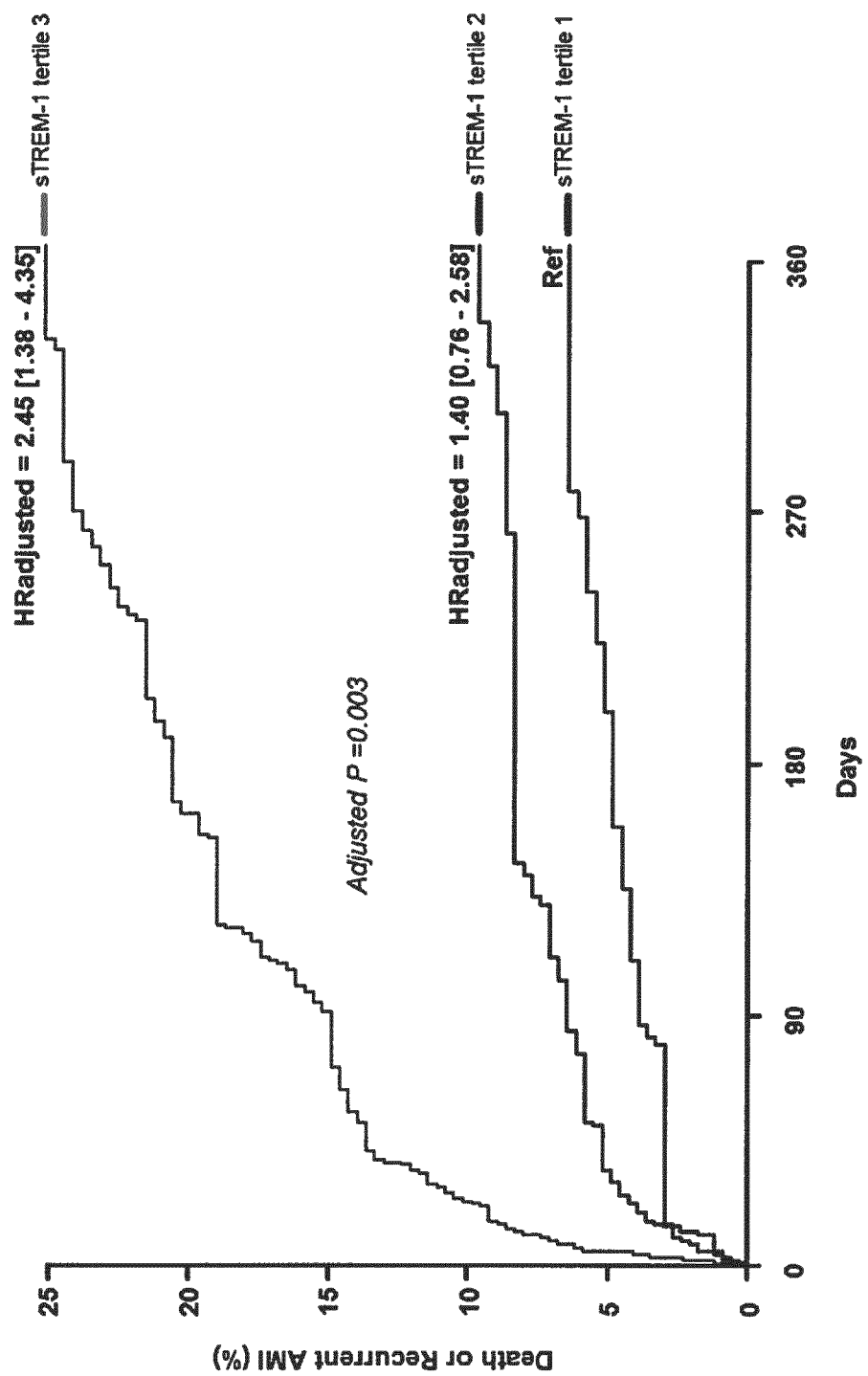
FIG. 1 is a graph representing the plasma concentration of Soluble TREM-1 and cardiovascular outcomes following myocardial infarction in the FAST-MI-2005 cohort.

(A) Adult male Balb/c mice (20-23 g) were subjected to myocardial ischemia and were randomly grouped (n=10 per group) to receive repeated LR12 (100 µg in 0.2 mL NaCl 0.9% once a day for 5 days) or scrambled-LR12 (100 µg in 0.2 mL NaCl 0.9% once a day for 5 days), i.p. injections. Blood samples was obtained at 24, 72 and 168 hours after cardiac ischemic event to measure plasma sTREM-1 levels. Physiologic baseline is calculated from dosage in healthy animals. N=10 per group and per timepoint.

(B) Atherosclerotic mice were randomized to receive LR12 (100 µg in 0.2 mL NaCl 0.9% once a day for 4 weeks) or scrambled-LR12 (100 µg in 0.2 mL NaCl 0.9% once a day for 4 weeks), i.p. injections. Blood samples were obtained at the end of the treatment (4 weeks) to assess sTREM-1 plasma concentrations. Physiologic baseline is calculated from dosage in healthy animals. N=10 per group.

EXAMPLES

The present invention is further illustrated by the following examples.
Methods
Study Population 1

The population and methods of the French registry of Acute ST-elevation and non-ST-elevation Myocardial Infarction (FAST-MI) have been described in detail in previous publications (Cambou, J.-P et al. 2007. Arch. Mal. Coeur Vaiss. 100: 524-534, Simon, T., et al. 2009. N. Engl. J. Med. 360: 363-375.). Briefly, all subjects>18 years of age were included in the registry if they had elevated serum markers of myocardial necrosis higher than twice the upper limit of normal for creatine kinase, creatine kinase-MB or elevated troponins, and either symptoms compatible with acute MI and/or electrocardiographic changes on at least two contiguous leads with pathologic Q waves (>0.04 sec)

and/or persisting ST elevation or depression>0.1 mV. The time from symptom onset to intensive care unit admission had to be <48 h. Subjects were managed according to usual practice; treatment was not affected by participation in the registry. Of the 374 centers in France that treated subjects with acute MI at that time, 223 (60%) participated in the registry and recruited 3670 patients. Among these, 100 centers recruited 1061 patients who contributed to the serum bank.

Their baseline characteristics were comparable to the overall population of the registry. More than 99% of subjects were Caucasians. Follow-up was collected through contacts with the subjects' physicians, the subjects themselves or their family, and registry offices of their birthplace. One-year follow-up was >99% complete. The study was reviewed by the Committee for the Protection of Human Subjects in Biomedical Research of Saint Antoine University Hospital and the data file was declared to the Commission Nationale Informatique et Libertés.

Study Population 2

A second confirmative study is used here, named FAST-MI-2010. This cohort has been described in detail in previous publications (Hanssen M et al. Heart. 2012 May; 98(9): 699-705). Briefly, all subjects>18 years of age were included in the registry if they had elevation of serum markers of myocardial necrosis (troponins or creatine kinase MB), with at least one of the following: symptoms compatible with myocardial ischaemia, development of new abnormal Q waves, ST-T changes compatible with myocardial ischaemia (ST segment elevation or depression, T wave inversion). The time from symptom onset to intensive care unit admission had to be <48 h. Subjects were managed according to usual practice; treatment was not affected by participation in the registry. 213 centers (76% of centers treating AMI patients at that time) participated in the registry and recruited 4169 patients, starting inclusion at 1 Oct. 2010. FAST-MI 2010 was set-up to conduct a new survey with similar objectives as the 2005 registry. One-year follow-up was >99% complete.

Blood Sampling and Measurements

Blood samples used for this study were recovered at the time of admission to the intensive care unit (<48 h from symptom onset). Blood samples were stored at −80° C. All samples were identified by number only and were analyzed in random order. Serum concentrations of sTREM-1 were determined by ELISA (TREM-1 Duo-Set, RnDsystems) using a detection limit at 46.9 pg/mL. In the first cohort (FAST-MI-2005), among the 1061 subjects who contributed to a bank, results for sTREM-1 levels were obtained for 1015 subjects (missing measures). In the second cohort FAST-MI-2010, results for sTREM-1 levels were obtained for 1293 subjects.

Mice serum levels of sTREM-1 were determined by ELISA (Mouse TREM-1 Quantikine ELISA Kit, RnDsystems) using a detection limit at 31.3 pg/mL.

Statistical Analysis

An outcome event was defined as all-cause death or non-fatal MI during the 2-year follow-up period. The primary endpoint, a composite of all-cause death and non-fatal MI defined as the episode index at inclusion, was adjudicated by a committee whose members were unaware of patients' medications, and blood measurements. Continuous variables are described as mean±SD and categorical variables as frequencies and percentages. Plasma levels of sTREM-1 and C-reactive protein were log-transformed to remove positive skewness, before being used as continuous variables. Baseline demographic and clinical characteristics, treatment factors, and therapeutic management during hospitalization were compared as pre-specified among the tertiles of sTREM-1 levels using $\chi 2$ or Fisher's exact tests for discrete variables, and by Wilcoxon signed-rank test or Kruskal-Wallis test for continuous variables. Tertiles of sTREM-1 levels were constructed based on data for the whole sample.

Survival curves according to sTREM-1 tertiles are estimated using the Kaplan-Meier estimator.

We used a multivariable Cox proportional hazards model to assess the independent prognostic value of variables with the primary endpoint during the 2-year follow up period. The multivariable model comprised sex, age, previous or current smoking, body mass index, family history of coronary disease, history of hypertension, prior acute MI, heart failure, renal failure, chronic obstructive pulmonary disease, diabetes, heart rate at admission, Killip class, left ventricular ejection fraction, hospital management (including reperfusion therapy, statins, beta-blockers, clopidogrel, diuretics, digitalis, heparin), and log C-reactive protein levels. The results are expressed as hazard ratios for Cox models with 95% confidence intervals (CIs). Sensitivity versus the false positive frequency (1-specificity) for cardiovascular outcomes during follow up associated with sTREM-1 levels was analysed by a receiver-operated characteristic (ROC) curve. The Youden index was calculated for sTREM-1 levels using the following formula: sensitivity+specificity−1; with the maximum value of the Youden index corresponding to the optimal cut-off point (Youden W J. Cancer. 1950; 3:32-35).

All statistical tests were two-sided and performed using the SAS software version 9.3.

Peptides

LR12 is a 12 amino-acids peptide (LQEEDTGEYGCV, SEQ ID NO: 4) known to specifically target TREM-1 ligand. It was chemically synthesized (Pepscan Presto BV, Lelystad, The Netherland) as Cter amidated peptide for in vivo assays. The correct peptides were obtained with >95% yields and were homogeneous after preparative purification, as confirmed by mass spectrometry and analytic reversed-phase high-performance liquid chromatography. These peptides were free of endotoxin. Corresponding scrambled peptide were similarly synthesized and served as control peptide (LR12-scrambled, composed of same amino acids than LR12 but in a randomized sequence known to not display TREM-1 inhibitory properties).

Animals

All procedures were approved by the local committee for care and use for laboratory animals and were performed according to international guidelines on animal experimentation. Mice and rats were obtained from the Charles River (Strasbourg, France).

Mouse Model of Myocardial Infarction

All procedures were performed on mice male C57BL/C ranging in age from 6-8 weeks. Mice were anesthetized by an intraperitoneal injection of xylazine (60 mg/kg) and fixed in supine position. The trachea was intubated and ventilated (the tidal volume was 200 µl/25 g and the respiratory rate was 120 breaths/min). After a left thoracotomy, the left coronary artery was identified and ligated with an 8-0 prolene surgical suture at 1.0 mm distal from tip of the left auricle. LAD occlusion was confirmed by a change in myocardial color from red to white in the ischemia area (Left ventricle). The chest was closed and the skin was sutured with 6-0 silk. The animals returned to their cage where they are supervised until their complete recovery.

Mice were randomized to receive or not peptides (daily ip injection for 5 days, 5 mg/kg) and were sacrificed after 24 h, 72 h, 168 h (n=6 per group) by anesthesia followed with pentobarbital sodium overdose for blood sampling.

Atherosclerosis in Mouse 12 and 24-weeks old male ApoE−/− mice were put on a fat (lipids 15%, cholesterol 1.25%, no cholate) or chow diet and were treated by daily intraperitoneal injection of peptides (100 μg/day). After 4 weeks of treatment, mice were sacrificed for blood sampling.

Results 1

Our objective was to assess the relationship between soluble TREM-1 levels and cardiovascular outcomes in patients enrolled in the French registry of Acute ST elevation or non-ST-elevation Myocardial Infarction (FAST-MI, NCT00673036) within 48 hours after an acute myocardial infarction. Serum levels of sTREM-1 were associated with the risk of all-cause death and recurrent MI at one and two years, with high level of sTREM-1 indicative of a worse outcome. Of the 1015 patients enrolled, 183 patients (18%) died or had an MI during the 2-year follow-up period.

Patients who died or had an MI during the follow-up were older (75±12 vs. 64±13 years) with a higher proportion of females (42 vs. 27%), than those without an outcome event. They also had a higher rate of hypertension, diabetes, prior heart failure, prior MI, prior stroke or transient ischemic event, chronic renal failure and chronic obstructive pulmonary disease.

They were less likely to be on statin therapy (68 vs. 81%), beta-blockers (50 vs. 76%), clopidogrel, heparin, but more likely to be on diuretics, or digoxin compared with patients without an outcome event during the follow-up. Patients who had an event were at higher risk of hospital death according to the GRACE (Global Registry of Acute Coronary Events) risk score and fewer patients had undergone coronary angioplasty PCI (43 vs. 73%) or thrombolysis (9 vs. 17%) during hospitalization.

Characteristics of patients according to their outcomes are listed in Table 1.

TABLE 1

| 2 years follow-up | Patients without outcome event n = 832 | Patients with outcome event n = 183 | p† |
|---|---|---|---|
| Demographic and risk factors | | | |
| Male Sex, No (%) | 605 (73%) | 107 (58%) | 0.0001 |
| Age, yr‡ | 64 ± 13 | 75 ± 12 | <0.0001 |
| Hypertension, No (%) | 483 (58%) | 147 (80%) | <0.0001 |
| Hypercholesterolemia, No (%) | 435 (52%) | 99 (54%) | 0.6562 |
| Diabetes mellitus, No (%) | 225 (27%) | 94 (51%) | <0.0001 |
| Family history of CAD, No (%) | 221 (27%) | 24 (13%) | 0.0001 |
| Previous or current smokers, No (%) | 484 (58%) | 77 (42%) | <0.0001 |
| Prior myocardial infarction, No (%) | 124 (15%) | 54 (30%) | <0.0001 |
| Prior PCI or CABG, No (%) | 133 (16%) | 44 (24%) | 0.0093 |
| Prior stroke or TIA, No (%) | 52 (6%) | 25 (14%) | 0.0006 |
| Prior Heart Failure, No (%) | 26 (3%) | 27 (15%) | <0.0001 |
| Prior Respiratory Failure, No (%) | 29 (3%) | 25 (14%) | <0.0001 |
| Chronic Renal Failure, No (%) | 25 (3%) | 26 (14%) | <0.0001 |
| Clinical Presentation | | | |
| Body mass index (kg/m²)‡ | 27 ± 5 | 26 ± 5 | 0.0232 |
| Systolic blood pressure at admission‡ | 141 ± 28 | 138 ± 31 | 0.1434 |
| Diastolic blood pressure at admission‡ | 81 ± 17 | 76 ± 17 | 0.0001 |
| Heart rate at admission‡ | 78 ± 20 | 86 ± 24 | <0.0001 |
| STEMI, No (%) | 456 (55%) | 73 (40%) | 0.0003 |
| Killip entree class = 2 or more, No (%) | 170 (21%) | 98 (55%) | <0.0001 |
| GRACE Score‡ | 158 ± 36 | 186 ± 35 | <0.0001 |
| Left ventricular ejection fraction‡ | 54 ± 12 | 47 ± 14 | <0.0001 |
| Baseline biological exams | | | |
| CRP (mg/l)‡ | 10.3 ± 14.2 | 16.0 ± 17.6 | <0.0001 |
| sTREM-1 (pg/mL)‡ | 330 ± 386 | 541 ± 633 | <0.0001 |
| In-hospital Management | | | |
| PCI, No (%) | 608 (73%) | 79 (43%) | <0.0001 |
| Thrombolysis, No (%) | 144 (17%) | 17 (9%) | 0.0075 |
| Coronary artery bypass surgery, No (%) | 31 (4%) | 6 (3%) | 0.7701 |
| Statins, No (%) | 674 (81%) | 124 (68%) | <0.0001 |
| Beta-blockers, No (%) | 635 (76%) | 92 (50%) | <0.0001 |
| Calcium Channel blockers, No (%) | 162 (19%) | 48 (26%) | 0.041 |
| ACE inhibitors or ARB, No (%) | 455 (55%) | 98 (54%) | 0.78 |
| Nitrated Derivatives, No (%) | 427 (51%) | 105 (57%) | 0.1376 |
| Aspirin, No (%) | 771 (93%) | 158 (86%) | 0.0054 |
| Clopidogrel, No (%) | 758 (91%) | 139 (76%) | <0.0001 |
| Heparin, No (%) | 702 (84%) | 138 (75%) | 0.0037 |

TABLE 1-continued

| 2 years follow-up | Patients without outcome event n = 832 | Patients with outcome event n = 183 | p† |
|---|---|---|---|
| Low Molecular Weight Heparin, No (%) | 543 (65%) | 96 (52%) | 0.0012 |
| Diuretics, No (%) | 225 (27%) | 118 (64%) | <0.0001 |
| Glycoprotein IIb/IIIa inhibitor, No (%) | 351 (41%) | 54 (30%) | 0.0015 |
| Digitalis glycosides, No (%) | 9 (1%) | 11 (6%) | <0.0001 |

†p is given by Wilcoxon signed-rank test or Kruskal-Wallis test (for continuous variables) and exact Pearson $x^2$ or Fisher test (for categorical variables), ‡mean ± sd.

ACE: angiotensin-converting enzyme inhibitors or ARB: angiotensin receptor blockers, PCI: percutanoeus coronary angioplasty, CABG: coronary artery bypass surgery.

Characteristics of patients according to sTREM-1 tertiles are listed in Table 2.

TABLE 2

| sTREM-1 (pg/ml) | Tertile 1 <212.4 | Tertile 2 [212.4-354[ | Tertile 3 ≥354 | p† |
|---|---|---|---|---|
| *Demographic and risk factors* | | | | |
| Male Sex, No (%) | 239 (71%) | 240 (71%) | 233 (69%) | 0.7677 |
| Age, yr‡ | 64 ± 12 | 65 ± 14 | 70 ± 14 | <0.0001 |
| Hypertension, No (%) | 200 (59%) | 190 (56%) | 240 (71%) | 0.0002 |
| Hypercholesterolemia, No (%) | 179 (53%) | 179 (53%) | 176 (52%) | 0.9489 |
| Diabetes mellitus, No (%) | 112 (33%) | 88 (26%) | 119 (35%) | 0.031 |
| Family history of CAD, No (%) | 87 (26%) | 96 (28%) | 62 (18%) | 0.006 |
| Previous or current smokers, No (%) | 187 (55%) | 207 (61%) | 167 (49%) | 0.0064 |
| Prior myocardial infarction, No (%) | 52 (15%) | 54 (16%) | 72 (21%) | 0.0872 |
| Prior PCI or CABG, No (%) | 55 (16%) | 59 (18%) | 63 (19%) | 0.7199 |
| Prior stroke or TIA, No (%) | 15 (4%) | 19 (6%) | 43 (13%) | <0.0001 |
| Prior Heart Failure, No (%) | 6 (2%) | 11 (3%) | 36 (11%) | <0.0001 |
| Prior Respiratory Failure, No (%) | 9 (3%) | 15 (4%) | 30 (9%) | 0.0011 |
| Chronic Renal Failure, No (%) | 4 (1%) | 6 (2%) | 41 (12%) | <0.0001 |
| *Clinical Presentation* | | | | |
| Body mass index (kg/m$^2$)‡ | 28 ± 5 | 27 ± 4 | 27 ± 5 | 0.0132 |
| Systolic blood pressure at admission‡ | 143 ± 28 | 140 ± 27 | 138 ± 31 | 0.0925 |
| Diastolic blood pressure at admission‡ | 81 ± 16 | 80 ± 16 | 79 ± 18 | 0.0471 |
| Heart rate at admission‡ | 75 ± 17 | 80 ± 23 | 83 ± 22 | <0.0001 |
| STEMI, No (%) | 172 (51%) | 181 (54%) | 176 (52%) | 0.7385 |
| Killip entree class = 2 or more, No (%) | 37 (11%) | 81 (24%) | 150 (45%) | <0.0001 |
| GRACE Score‡ | 151 ± 31 | 161 ± 37 | 177 ± 38 | <0.0001 |
| Left ventricular ejection fraction‡ | 56 ± 11 | 53 ± 12 | 49 ± 14 | <0.0001 |
| *Baseline biological exams* | | | | |
| CRP (mg/l)‡ | 7.1 ± 9.3 | 11.7 ± 16 | 15.3 ± 17.4 | <0.0001 |
| sTREM-1 (pg/mL)‡ | 139 ± 48 | 278 ± 40 | 686 ± 660 | <0.0001 |
| *In-hospital Management* | | | | |
| PCI, No (%) | 251 (74%) | 241 (72%) | 195 (58%) | <0.0001 |
| Thrombolysis, No (%) | 48 (14%) | 58 (17%) | 55 (16%) | 0.5602 |
| Coronary artery bypass surgery, No (%) | 18 (5%) | 7 (2%) | 12 (4%) | 0.0803 |
| Statins, No (%) | 272 (80%) | 274 (81%) | 252 (74%) | 0.0586 |
| Beta-blockers, No (%) | 258 (76%) | 247 (73%) | 222 (65%) | 0.0064 |
| Calcium Channel blockers, No (%) | 66 (19%) | 65 (19%) | 79 (23%) | 0.3459 |

TABLE 2-continued

| sTREM-1 (pg/ml) | Tertile 1 <212.4 | Tertile 2 [212.4-354[ | Tertile 3 ≥354 | p† |
|---|---|---|---|---|
| ACE inhibitors or ARB, No (%) | 171 (50%) | 184 (55%) | 198 (58%) | 0.1143 |
| Nitrated Derivatives, No (%) | 170 (50%) | 176 (52%) | 186 (55%) | 0.4674 |
| Aspirin, No (%) | 316 (93%) | 311 (92%) | 302 (89%) | 0.1287 |
| Clopidogrel, No (%) | 313 (92%) | 298 (88%) | 286 (84%) | 0.0053 |
| Heparin, No (%) | 289 (85%) | 289 (86%) | 262 (77%) | 0.0047 |
| Low Molecular Weight Heparin, No (%) | 238 (70%) | 227 (67%) | 174 (51%) | <0.0001 |
| Diuretics, No (%) | 63 (19%) | 106 (31%) | 174 (51%) | <0.0001 |
| Glycoprotein IIb/IIIa inhibitor, No (%) | 139 (41%) | 148 (44%) | 118 (35%) | 0.0473 |
| Digitalis glycosides, No (%) | 1 (0.4%) | 8 (2%) | 11 (3%) | 0.0178 |

†p is given by Wilcoxon signed-rank test or Kruskal-Wallis test (for continuous variables) and exact Pearson $x^2$ or Fisher test (for categorical variables),
‡mean ± sd.
ACE: angiotensin-converting enzyme inhibitors or ARB: angiotensin receptor blockers,
PCI: percutanoeus coronary angioplasty,
CABG: coronary artery bypass surgery.

The level of sTREM-1 (pg/ml) was measured (Table 3).

The median level of sTREM-1 for the entire population was 273 pg/mL (range 50-7069; first tertile<212.4 pg/mL, n=339; third tertile>354 pg/mL, n=339).

TABLE 3

| | No. at Risk | | | | | | | | |
|---|---|---|---|---|---|---|---|---|---|
| | Days | | | | | | | | |
| | 0 | 90 | 180 | 270 | 360 | 450 | 540 | 630 | 720 |
| sTREM-1 tertile 1 | 339 | 319 | 314 | 306 | 302 | 298 | 295 | 282 | 238 |
| sTREM-1 tertile 2 | 337 | 310 | 304 | 296 | 292 | 288 | 283 | 258 | 234 |
| sTREM-1 tertile 3 | 339 | 281 | 263 | 251 | 243 | 237 | 232 | 206 | 176 |

The probability of outcome events as a function of the baseline sTREM-1 level is presented in FIG. 1.

At 1 year, event rates for death and MI was 6% for the first tertile, 9% for the second tertile, and 24% for the third tertile.

At 2 years, event rates for death and MI was 9% for the first tertile, 14% for the second tertile, and 31% for the third tertile.

The adjusted HR of death and recurrent MI during the 2-year follow-up associated with an increase of 1 unit pg/mL of log (sTREM-1) was 1.70 (95% CI 1.33-2.17; p<0.0001).

We also tested for trend over tertiles of sTREM-1 to examine the association over a wider range of sTREM-1 levels. Compared with tertile 1, chosen as a reference, adjusted HR was 1.38 (95% CI 0.83-2.28) and 2.08 (95% CI 1.28-3.39) for tertile 2 and tertile 3, respectively (overall p=0.006). The Cochran-Armitage trend test was significant (p<0.0001).

Figure 2:
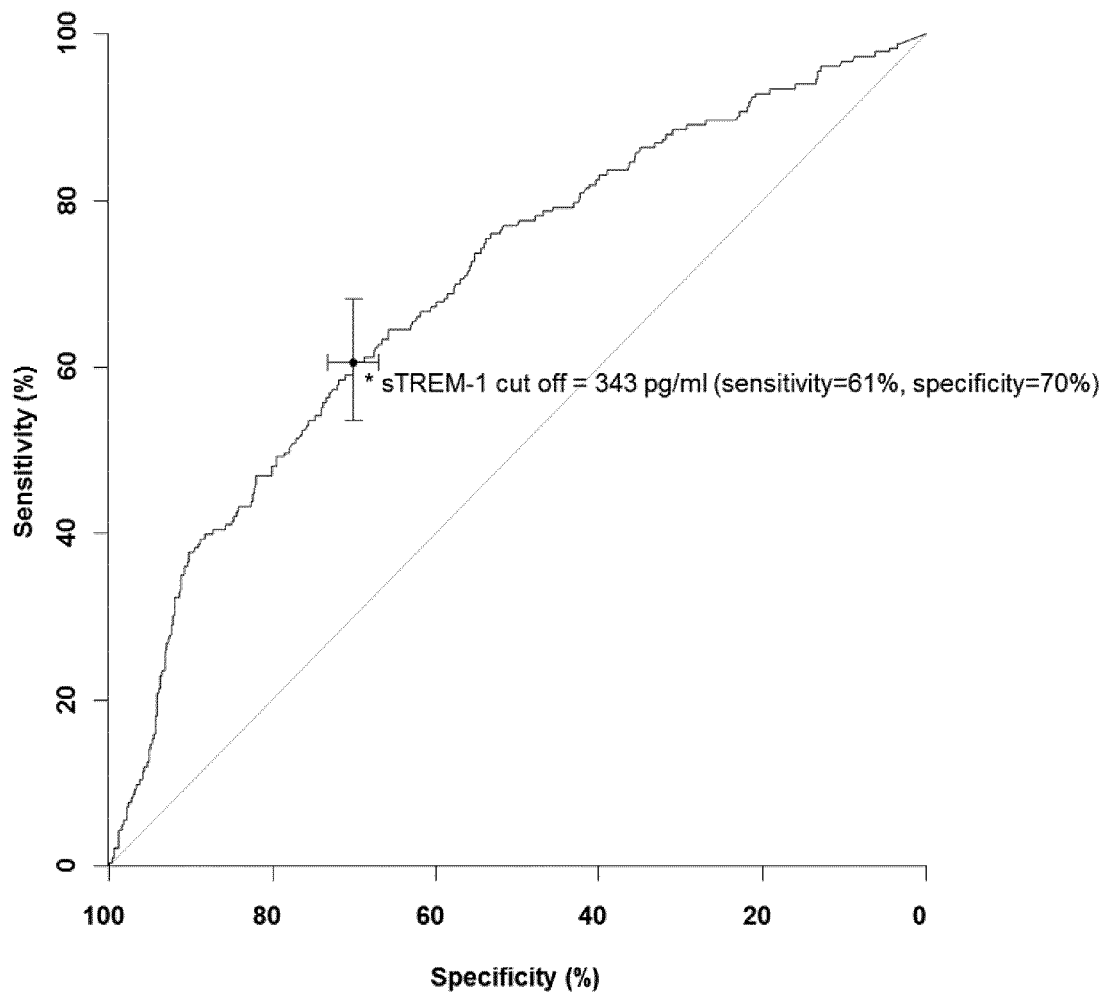
FIG. 2 is a graph representing the area under the ROC curve (AUC) of sTREM-1 levels in the adjusted model in the FAST-MI-2005 cohort.

The area under the ROC curve (AUC) of sTREM-1 levels in the adjusted model that accurately predicted cardiovascular outcomes after 2-year follow up was 0.847 (FIG. 2).

Considering the higher values of sensitivity combined with the lower values of (1-specificity), the best cut-off for sTREM-1 level using the Youden index was 343 pg/mL (sensitivity=0.61 and specificity=0.70).

Results 2

Results with the first cohort FAST-MI-2005 were confirmed with a second cohort FAST-MI-2010. FAST-MI 2010 was set-up to conduct a new survey with similar criteria and objectives as the 2005 registry. In this cohort, sTREM-1 levels were associated with the risk of all-cause death at one year following an acute myocardial infarction.

Characteristics of patients according to sTREM-1 tertiles are listed in Table 4 and Table 5. The range of sTREM-1 is 112 to 7038, first tertile<264.552 pg/mL n=430, third tertile>444.287 pg/mL n=432).

Figure 3:
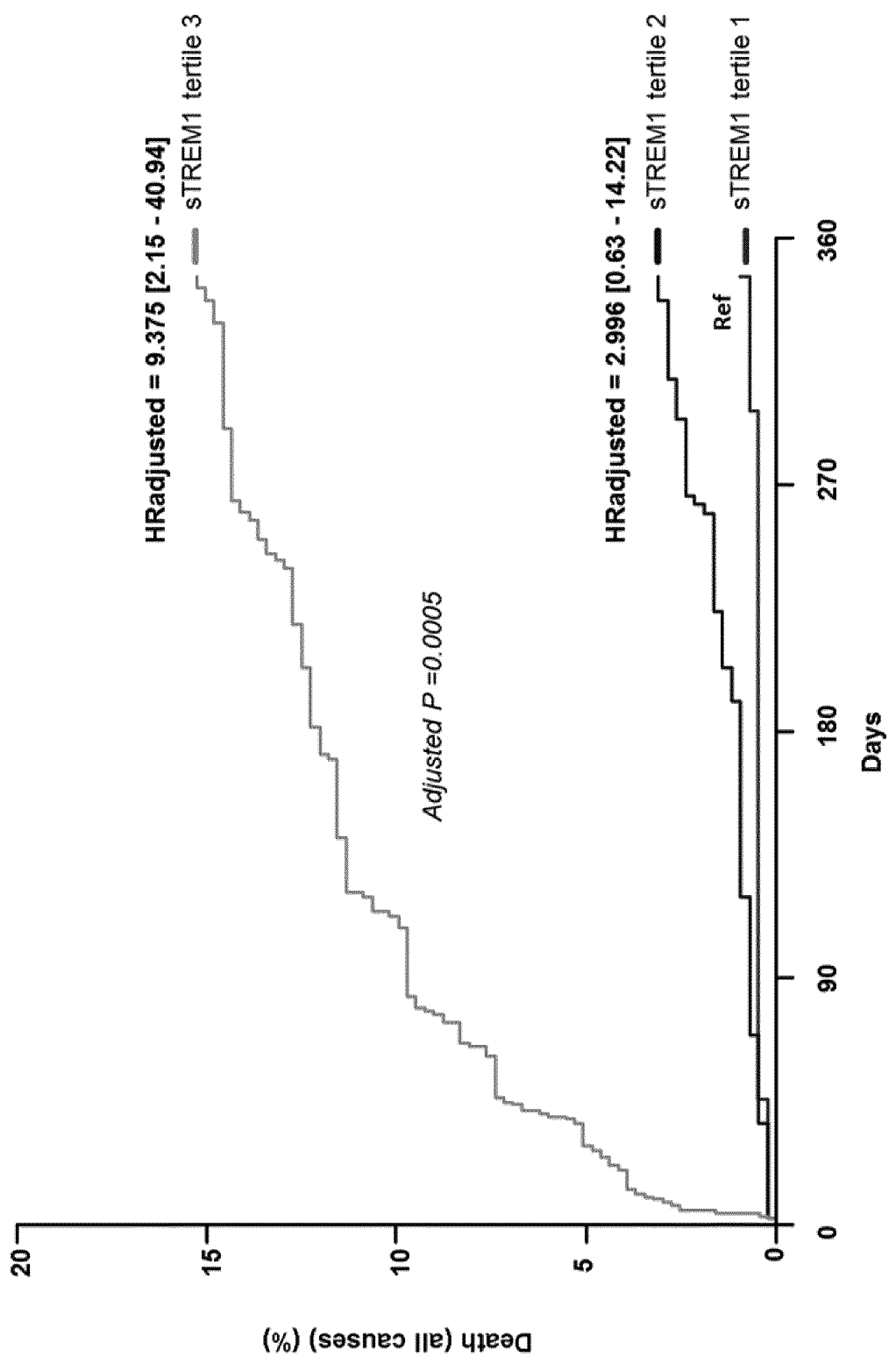
FIG. 3 is a graph representing the plasma concentration of Soluble TREM-1 and death following myocardial infarction in the FAST-MI-2010 cohort.

The probability of all-cause death as a function of the baseline sTREM-1 level is presented in FIG. 3. The adjusted HR of death during the 1-year follow-up associated with an increase of 1 unit pg/mL of log (sTREM-1) was 3.784 (95% CI 2.440-5.869; p<0.0001).

Compared with tertile 1, chosen as a reference, adjusted HR was 2.996 (95% CI 0.631-14.220) and 9.375 (95% CI 2.147-40.936) for tertile 2 and tertile 3, respectively (overall p=0.0005). The Cochran-Armitage trend test was significant (p<0.0001).

TABLE 4

| | No. at Risk | | | | |
|---|---|---|---|---|---|
| | Days | | | | |
| | 0 | 90 | 180 | 270 | 360 |
| sTREM-1 tertile 1 | 430 | 423 | 423 | 423 | 421 |
| sTREM-1 tertile 2 | 431 | 416 | 414 | 407 | 405 |
| sTREM-1 tertile 3 | 432 | 390 | 379 | 370 | 366 |

TABLE 5

| sTREM-1 (pg/ml) | Tertile 1 <264.552 | Tertile 2 [264.552-444.287[ | Tertile 3 ≥444.287 | p† |
|---|---|---|---|---|
| Demographic and risk factors | | | | |
| Male Sex, No (%) | 325 (76%) | 313 (73%) | 312 (72%) | 0.4753 |
| Age, yr‡ | 61 ± 12 | 63 ± 14 | 69 ± 15 | <0.0001 |
| Hypertension, No (%) | 196 (46%) | 208 (48%) | 275 (64%) | <0.0001 |
| Hypercholesterolemia, No (%) | 187 (44%) | 188 (44%) | 179 (41%) | 0.7676 |
| Diabetes mellitus, No (%) | 78 (18%) | 73 (17%) | 108 (25%) | 0.0061 |
| Family history of CAD, No (%) | 152 (35%) | 130 (30%) | 71 (16%) | <0.0001 |
| Current smokers, No (%) | 138 (32%) | 189 (441%) | 168 (39%) | 0.0017 |
| Prior myocardial infarction, No (%) | 50 (12%) | 61 (14%) | 74 (17%) | 0.0695 |
| Prior stroke or TIA, No (%) | 14 (3%) | 13 (3%) | 24 (6%) | 0.1066 |
| Prior Heart Failure, No (%) | 4 (1%) | 12 (3%) | 26 (6%) | 0.0001 |
| Prior Respiratory Failure, No (%) | 14 (3%) | 17 (4%) | 38 (9%) | 0.0004 |
| Chronic Renal Failure, No (%) | 2 (0.5%) | 3 (1%) | 48 (11%) | <0.0001 |
| Clinical Presentation | | | | |
| Body mass index (kg/m$^2$)‡ | 27 ± 4 | 27 ± 5 | 26 ± 5 | 0.011 |
| Systolic blood pressure at admission‡ | 148 ± 27 | 145 ± 28 | 143 ± 30 | 0.0153 |
| Heart rate at admission‡ | 77 ± 18 | 78 ± 18 | 80 ± 22 | 0.0527 |
| STEMI, No (%) | 235 (55%) | 238 (55%) | 232 (54%) | 0.9029 |
| Killip entree class = 2 or more, No (%) | 45 (10%) | 50 (12%) | 146 (34%) | <0.0001 |
| GRACE Score‡ | 126 ± 28 | 133 ± 31 | 156 ± 39 | <0.0001 |
| Left ventricular ejection fraction‡ | 55 ± 10 | 53 ± 11 | 48 ± 12 | <0.0001 |
| Baseline biological exams | | | | |
| CRP (mg/l)‡ | 9 ± 26 | 12 ± 25 | 28 ± 51 | <0.0001 |
| sTREM-1 (pg/mL)‡ | 173 ± 64 | 346 ± 50 | 773 ± 521 | <0.0001 |
| In-hospital Management | | | | |
| PCI, No (%) | 351 (82%) | 346 (80%) | 310 (72%) | 0.0008 |
| Coronary artery bypass surgery, No (%) | 18 (4%) | 11 (3%) | 13 (3%) | 0.3779 |
| Statins, No (%) | 390 (91%) | 400 (93%) | 364 (84%) | 0.0001 |
| Beta-blockers, No (%) | 379 (88%) | 359 (83%) | 316 (73%) | <0.0001 |
| Calcium Channel blockers, No (%) | 98 (23%) | 124 (29%) | 107 (25%) | 0.1216 |
| ACE inhibitors or ARB, No (%) | 295 (69%) | 298 (69%) | 255 (59%) | 0.002 |
| Nitrated Derivatives, No (%) | 215 (50%) | 223 (52%) | 190 (44%) | 0.0571 |
| Aspirin, No (%) | 420 (98%) | 424 (98%) | 414 (96%) | 0.0593 |
| Clopidogrel, No (%) | 338 (79%) | 335 (78%) | 340 (79%) | 0.9291 |
| Low Molecular Weight Heparin, No (%) | 269 (63%) | 262 (61%) | 215 (50%) | 0.0002 |
| Diuretics, No (%) | 79 (18%) | 99 (23%) | 183 (42%) | <0.0001 |
| Glycoprotein IIb/IIIa inhibitor, No (%) | 166 (39%) | 188 (44%) | 120 (28%) | <0.0001 |
| Digitalis glycosides, No (%) | 2 (0.5%) | 1 (0.2%) | 7 (2%) | 0.0854 |

†p is given by Wilcoxon signed-rank test or Kruskal-Wallis test (for continuous variables) and exact Pearson $x^2$ or Fisher test (for categorical variables),
‡mean ± sd.
ACE: angiotensin-converting enzyme inhibitors or ARB: angiotensin receptor blockers,
PCI: percutanoeus coronary angioplasty,
CABG: coronary artery bypass surgery.

Results 3

Our second objective was to assess whether a treatment could impact plasma levels of sTREM-1. Atherosclerotic mice (24 weeks old ApoE−/− mice under fat diet) were treated by LR12 peptide, which targets TREM-1 ligand, or a control peptide LR12-scrambled. We show that sTREM-1 levels was elevated after 4 weeks of treatment (311.8 pg/mL) and that LR12 treatment is linked to a decrease in sTREM-1 plasma concentration (189.8 pg/mL) (FIG. 4B).

We also show in infarcted mice that sTREM-1 levels were decreased by LR12 treatment 24 and 72 hours after an ischemic event (FIG. 4A).

Since LR12 administration is linked to a better outcome after a cardiac ischemic event as well as during atherosclerosis (data not shown), these results suggest that dosage of sTREM-1 could be used in combination with a treatment to evaluate the progression of the disease.

The invention claimed is:

1. A method for preventing a cardiovascular event in a subject determined to be at risk of having a cardiovascular event, wherein said cardiovascular event is selected from the group consisting of sudden cardiac death, an acute coronary syndrome and a non-cardiac acute arteriovascular event, said method comprising:
   determining a subject to be at risk of having a cardiovascular event by:
      measuring the expression level of soluble Triggering Receptors Expressed on Myeloid cells-1 (sTREM-1) in a sample from the subject, wherein said expression level is the expression level of mRNA or the expression level of protein;
      comparing the sTREM-1 expression level measured in the sample from the subject to a reference value; and
      determining the subject to be at risk of having a cardiovascular event, wherein a sTREM-1 expression level higher than the reference value is indicative of being at risk of having a cardiovascular event;
   preventing a cardiovascular event in the subject determined to be at risk of having a cardiovascular event by administering to said subject a therapy for preventing a cardiovascular event, wherein said therapy is a modulator of TREM-1 function, activity or expression.

2. The method according to claim 1, wherein the sample is a blood sample.

3. The method according to claim 1, wherein said acute coronary syndrome is myocardial infarction.

4. The method according to claim 1, wherein the reference value is the expression level of sTREM-1 in a control sample derived from one or more subjects who are healthy.

5. The method according to claim 1, wherein the subject has been previously diagnosed with a cardiovascular event.

6. The method according to claim 1, wherein the modulator of TREM-1 function, activity or expression is selected from the group consisting of antibodies directed to TREM-1, sTREM-1, TREM-1 ligand or sTREM-1 ligand; small molecules inhibiting the function, activity or expression of TREM-1; peptides inhibiting the function, activity or expression of TREM-1; siRNAs directed to TREM-1; shRNAs directed to TREM-1; antisense oligonucleotide directed to TREM-1; ribozymes directed to TREM-1 and aptamers of TREM-1.

7. The method according to claim 1, wherein the modulator of TREM-1 function, activity or expression is a peptide targeting TREM-1 ligand.

8. The method according to claim 1, wherein the modulator of TREM-1 function, activity or expression is a peptide comprising amino acid sequence SEQ ID NO: 4.

9. The method according to claim 1, wherein the cardiovascular event is selected from the group consisting of sudden cardiac death, myocardial infarction, aneurysms or aneurysm progression, and stroke.

* * * * *

SEQUENCE LISTING

<160> NUMBER OF SEQ ID NOS: 4

<210> SEQ ID NO 1
<211> LENGTH: 234
<212> TYPE: PRT
<213> ORGANISM: Homo sapiens
<220> FEATURE:
<223> OTHER INFORMATION: TREM-1

<400> SEQUENCE: 1

Met Arg Lys Thr Arg Leu Trp Gly Leu Leu Trp Met Leu Phe Val Ser
1               5                   10                  15

Glu Leu Arg Ala Ala Thr Lys Leu Thr Glu Glu Lys Tyr Glu Leu Lys
            20                  25                  30

Glu Gly Gln Thr Leu Asp Val Lys Cys Asp Tyr Thr Leu Glu Lys Phe
            35                  40                  45

Ala Ser Ser Gln Lys Ala Trp Gln Ile Ile Arg Asp Gly Glu Met Pro
50                  55                  60

Lys Thr Leu Ala Cys Thr Glu Arg Pro Ser Lys Asn Ser His Pro Val
65                  70                  75                  80

Gln Val Gly Arg Ile Ile Leu Glu Asp Tyr His Asp His Gly Leu Leu
                85                  90                  95

Arg Val Arg Met Val Asn Leu Gln Val Glu Asp Ser Gly Leu Tyr Gln
                100                 105                 110

Cys Val Ile Tyr Gln Pro Pro Lys Glu Pro His Met Leu Phe Asp Arg
                115                 120                 125

Ile Arg Leu Val Val Thr Lys Gly Phe Ser Gly Thr Pro Gly Ser Asn
130                 135                 140

Glu Asn Ser Thr Gln Asn Val Tyr Lys Ile Pro Pro Thr Thr Thr Lys
145                 150                 155                 160

Ala Leu Cys Pro Leu Tyr Thr Ser Pro Arg Thr Val Thr Gln Ala Pro
                165                 170                 175

Pro Lys Ser Thr Ala Asp Val Ser Thr Pro Asp Ser Glu Ile Asn Leu
                180                 185                 190

Thr Asn Val Thr Asp Ile Ile Arg Val Pro Val Phe Asn Ile Val Ile
                195                 200                 205

Leu Leu Ala Gly Gly Phe Leu Ser Lys Ser Leu Val Phe Ser Val Leu
                210                 215                 220

Phe Ala Val Thr Leu Arg Ser Phe Val Pro
225                 230

<210> SEQ ID NO 2
<211> LENGTH: 185
<212> TYPE: PRT
<213> ORGANISM: Artificial Sequence
<220> FEATURE:
<223> OTHER INFORMATION: sTREM-1

<400> SEQUENCE: 2

Ala Thr Lys Leu Thr Glu Glu Lys Tyr Glu Leu Lys Glu Gly Gln Thr
1               5                   10                  15

Leu Asp Val Lys Cys Asp Tyr Thr Leu Glu Lys Phe Ala Ser Ser Gln
            20                  25                  30

Lys Ala Trp Gln Ile Ile Arg Asp Gly Glu Met Pro Lys Thr Leu Ala
            35                  40                  45

Cys Thr Glu Arg Pro Ser Lys Asn Ser His Pro Val Gln Val Gly Arg
50                  55                  60

Ile Ile Leu Glu Asp Tyr His Asp His Gly Leu Leu Arg Val Arg Met
65                  70                  75                  80

Val Asn Leu Gln Val Glu Asp Ser Gly Leu Tyr Gln Cys Val Ile Tyr
                85                  90                  95

Gln Pro Pro Lys Glu Pro His Met Leu Phe Asp Arg Ile Arg Leu Val
                100                 105                 110

Val Thr Lys Gly Phe Ser Gly Thr Pro Gly Ser Asn Glu Asn Ser Thr
                115                 120                 125

```
Gln Asn Val Tyr Lys Ile Pro Pro Thr Thr Lys Ala Leu Cys Pro
        130                 135                 140

Leu Tyr Thr Ser Pro Arg Thr Val Thr Gln Ala Pro Pro Lys Ser Thr
145                 150                 155                 160

Ala Asp Val Ser Thr Pro Asp Ser Glu Ile Asn Leu Thr Asn Val Thr
                165                 170                 175

Asp Ile Ile Arg Val Pro Val Phe Asn
            180                 185

<210> SEQ ID NO 3
<211> LENGTH: 175
<212> TYPE: PRT
<213> ORGANISM: Artificial Sequence
<220> FEATURE:
<223> OTHER INFORMATION: sTREM-1

<400> SEQUENCE: 3

Leu Lys Glu Gly Gln Thr Leu Asp Val Lys Cys Asp Tyr Thr Leu Glu
1               5                   10                  15

Lys Phe Ala Ser Ser Gln Lys Ala Trp Gln Ile Ile Arg Asp Gly Glu
            20                  25                  30

Met Pro Lys Thr Leu Ala Cys Thr Glu Arg Pro Ser Lys Asn Ser His
        35                  40                  45

Pro Val Gln Val Gly Arg Ile Ile Leu Glu Asp Tyr His Asp His Gly
    50                  55                  60

Leu Leu Arg Val Arg Met Val Asn Leu Gln Val Glu Asp Ser Gly Leu
65                  70                  75                  80

Tyr Gln Cys Val Ile Tyr Gln Pro Pro Lys Glu Pro His Met Leu Phe
                85                  90                  95

Asp Arg Ile Arg Leu Val Val Thr Lys Gly Phe Ser Gly Thr Pro Gly
            100                 105                 110

Ser Asn Glu Asn Ser Thr Gln Asn Val Tyr Lys Ile Pro Pro Thr Thr
        115                 120                 125

Thr Lys Ala Leu Cys Pro Leu Tyr Thr Ser Pro Arg Thr Val Thr Gln
    130                 135                 140

Ala Pro Pro Lys Ser Thr Ala Asp Val Ser Thr Pro Asp Ser Glu Ile
145                 150                 155                 160

Asn Leu Thr Asn Val Thr Asp Ile Ile Arg Val Pro Val Phe Asn
                165                 170                 175

<210> SEQ ID NO 4
<211> LENGTH: 12
<212> TYPE: PRT
<213> ORGANISM: Artificial Sequence
<220> FEATURE:
<223> OTHER INFORMATION: LR12

<400> SEQUENCE: 4

Leu Gln Glu Glu Asp Thr Gly Glu Tyr Gly Cys Val
1               5                   10
```